(12) United States Patent
Azuma

(10) Patent No.: US 10,509,309 B2
(45) Date of Patent: *Dec. 17, 2019

(54) POLYARYLATE RESIN AND ELECTROPHOTOGRAPHIC PHOTOSENSITIVE MEMBER

(71) Applicant: KYOCERA Document Solutions Inc., Osaka (JP)

(72) Inventor: Jun Azuma, Osaka (JP)

(73) Assignee: KYOCERA Document Solutions Inc., Osaka (JP)

(*) Notice: Subject to any disclaimer, the term of this patent is extended or adjusted under 35 U.S.C. 154(b) by 12 days.

This patent is subject to a terminal disclaimer.

(21) Appl. No.: 15/899,400

(22) Filed: Feb. 20, 2018

(65) Prior Publication Data

US 2018/0246402 A1    Aug. 30, 2018

(30) Foreign Application Priority Data

Feb. 28, 2017    (JP) .................................. 2017-036065

(51) Int. Cl.

| | | |
|---|---|---|
| C08G 81/00 | (2006.01) | |
| G03C 1/795 | (2006.01) | |
| C08L 67/02 | (2006.01) | |
| G03C 1/06 | (2006.01) | |
| C08G 65/38 | (2006.01) | |
| C07C 211/01 | (2006.01) | |
| C08G 63/40 | (2006.01) | |
| G03G 5/05 | (2006.01) | |
| G03G 5/06 | (2006.01) | |
| C08G 63/189 | (2006.01) | |
| C08G 63/195 | (2006.01) | |
| C08L 101/00 | (2006.01) | |
| C07C 211/54 | (2006.01) | |

(52) U.S. Cl.
CPC .......... *G03C 1/7954* (2013.01); *C07C 211/01* (2013.01); *C08G 63/189* (2013.01); *C08G 63/195* (2013.01); *C08G 63/40* (2013.01); *C08G 65/38* (2013.01); *C08G 81/00* (2013.01); *C08L 67/025* (2013.01); *C08L 101/00* (2013.01); *G03C 1/06* (2013.01); *G03G 5/056* (2013.01); *G03G 5/0614* (2013.01); *G03G 5/0672* (2013.01); *C07C 211/54* (2013.01)

(58) Field of Classification Search
CPC ....... G03C 1/7954; G03C 1/06; C08L 67/025; C08G 81/00; C08G 65/38; C08G 63/189; C08G 63/40; C08G 63/195; C07C 211/01; C07C 211/54; C03G 5/056; C03G 5/0614; C03G 5/0672

See application file for complete search history.

(56) References Cited

U.S. PATENT DOCUMENTS

| | | | |
|---|---|---|---|
| 7,090,952 B2 | 8/2006 | Azuma et al. | |
| 2004/0101771 A1 | 5/2004 | Azuma et al. | |
| 2006/0157672 A1* | 7/2006 | Mazaki et al. | C08G 63/91 252/299.01 |
| 2019/0025720 A1* | 1/2019 | Azuma et al. | G03G 5/0618 |

FOREIGN PATENT DOCUMENTS

| | | |
|---|---|---|
| JP | H09-124781 A | 5/1997 |
| JP | 2004-177703 A | 6/2004 |
| JP | 2005-189716 A | 7/2005 |

OTHER PUBLICATIONS

An Office Action dated by the Japanese Patent Office on Aug. 20, 2019, which corresponds to Japanese Patent Application No. 2017-036065 and is related to U.S. Appl. No. 15/899,400.

* cited by examiner

*Primary Examiner* — Nathan M Nutter

(74) *Attorney, Agent, or Firm* — Studebaker & Brackett PC

(57) ABSTRACT

A polyarylate resin is represented by general formula (1) shown below. In general formula (1), $R^1$ represents a hydrogen atom or methyl group. $R^2$ and $R^3$ each represent a hydrogen atom or an alkyl group having a carbon number of at least 1 and no greater than 4. $R^2$ and $R^3$ are not the same as one another. When $R^1$ represents a hydrogen atom, $R^2$ and $R^3$ are not bonded to one another. When $R^1$ represents a methyl group, $R^2$ and $R^3$ are optionally bonded to one another to form a ring. r and s each represent a number greater than or equal to 0 and less than or equal to 49. t and u each represent a number greater than or equal to 1 and less than or equal to 50. r+s+t+u=100. r+t=s+u.

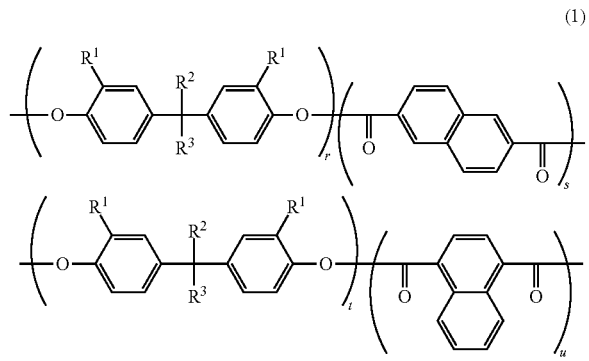

(1)

11 Claims, 1 Drawing Sheet

POLYARYLATE RESIN AND ELECTROPHOTOGRAPHIC PHOTOSENSITIVE MEMBER

INCORPORATION BY REFERENCE

The present application claims priority under 35 U.S.C. § 119 to Japanese Patent Application No. 2017-036065, filed on Feb. 28, 2017. The contents of this application are incorporated herein by reference in their entirety.

BACKGROUND

The present disclosure relates to polyarylate resins and electrophotographic photosensitive members.

Electrophotographic photosensitive members are used as image bearing members of electrophotographic image forming apparatuses (for example, printers or multifunction peripherals). The electrophotographic photosensitive members each include a photosensitive layer. The electrophotographic photosensitive members used in electrophotographic image forming apparatuses for example include single-layer electrophotographic photosensitive members and multi-layer electrophotographic photosensitive members. The single-layer electrophotographic photosensitive members each include a photosensitive layer having a charge generation function and a charge transport function. The multi-layer electrophotographic photosensitive members each include, as a photosensitive layer, a charge generating layer having a charge generation function and a charge transport layer having a charge transport function.

An exemplary known polyarylate resin includes a repeating unit represented by chemical formula (E-1) shown below. Furthermore, a known electrophotographic photosensitive member contains the polyarylate resin.

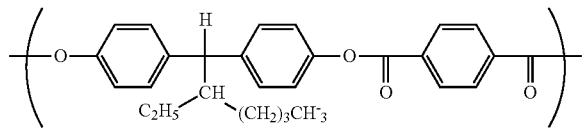

(E-1)

SUMMARY

A polyarylate resin according to an aspect of the present disclosure is represented by general formula (1) shown below.

no greater than 4. $R^2$ and $R^3$ are not the same as one another. When $R^1$ represents a hydrogen atom, $R^2$ and $R^3$ are not bonded to one another. When $R^1$ represents a methyl group, $R^2$ and $R^3$ are optionally bonded to one another to form a ring. r and s each represent a number greater than or equal to 0 and less than or equal to 49. t and u each represent a number greater than or equal to 1 and less than or equal to 50. $r+s+t+u=100$. $r+t=s+u$.

An electrophotographic photosensitive member according to another aspect of the present disclosure includes a conductive substrate and a photosensitive layer. The photosensitive layer contains a charge generating material, a hole transport material, and a binder resin. The binder resin includes the above-described polyarylate resin.

DETAILED DESCRIPTION

Figure 1A:
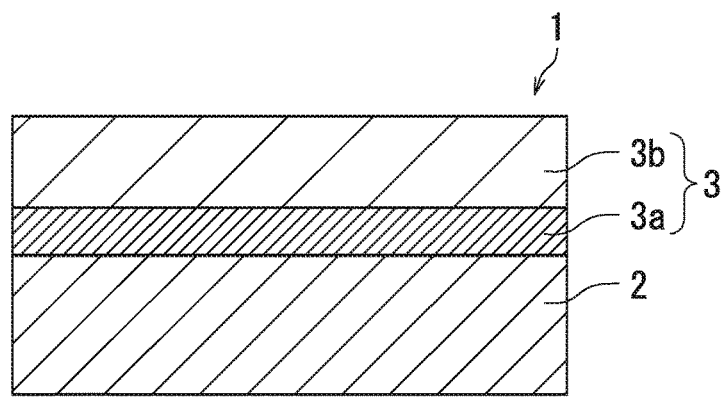
FIGS. 1A, 1B, and 1C are each a schematic cross-sectional view illustrating an example of a structure of an electrophotographic photosensitive member according to a second embodiment of the present disclosure.

The following describes embodiments of the present disclosure in detail. However, the present disclosure is not in any way limited by the following embodiments and appropriate changes may be made when practicing the present disclosure so long as such changes do not deviate from the intended scope of the present disclosure. Although description is omitted as appropriate in some instances in order to avoid repetition, such omission does not limit the essence of the present disclosure. Hereinafter, the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof.

Hereinafter, an alkyl group having a carbon number of at least 1 and no greater than 8, an alkyl group having a carbon number of at least 1 and no greater than 6, an alkyl group having a carbon number of at least 1 and no greater than 4, an alkyl group having a carbon number of at least 1 and no greater than 3, an alkoxy group having a carbon number of at least 1 and no greater than 8, an alkoxy group having a carbon number of at least 1 and no greater than 4, a cycloalkane having a carbon number of at least 5 and no

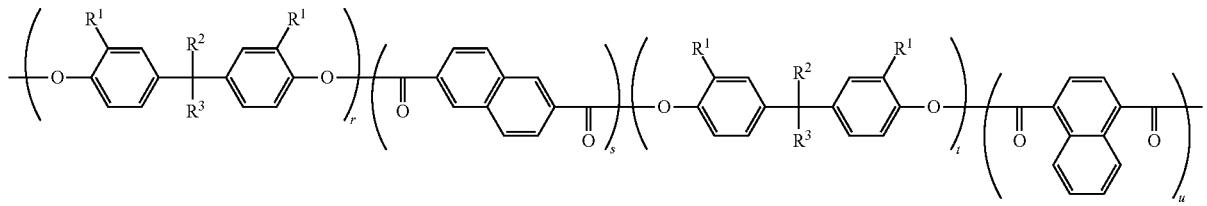

(1)

In general formula (1), $R^1$ represents a hydrogen atom or a methyl group. $R^2$ and $R^3$ each represent a hydrogen atom or an alkyl group having a carbon number of at least 1 and greater than 7, and a cycloalkylidene group having a carbon number of at least 5 and no greater than 7 each refer to the following.

An alkyl group having a carbon number of at least 1 and no greater than 8 as used herein refers to an unsubstituted straight chain or branched chain alkyl group. Examples of the alkyl group having a carbon number of at least 1 and no greater than 8 include a methyl group, an ethyl group, a propyl group, an isopropyl group, an n-butyl group, an s-butyl group, a t-butyl group, a pentyl group, an isopentyl group, a neopentyl group, a hexyl group, a heptyl group, and an octyl group.

An alkyl group having a carbon number of at least 1 and no greater than 6 as used herein refers to an unsubstituted straight chain or branched chain alkyl group. Examples of the alkyl group having a carbon number of at least 1 and no greater than 6 include a methyl group, an ethyl group, a propyl group, an isopropyl group, an n-butyl group, an s-butyl group, a t-butyl group, a pentyl group, an isopentyl group, a neopentyl group, and a hexyl group.

An alkyl group having a carbon number of at least 1 and no greater than 4 as used herein refers to an unsubstituted straight chain or branched chain alkyl group. Examples of the alkyl group having a carbon number of at least 1 and no greater than 4 include a methyl group, an ethyl group, a propyl group, an isopropyl group, an n-butyl group, an s-butyl group, and a t-butyl group.

An alkyl group having a carbon number of at least 1 and no greater than 3 as used herein refers to an unsubstituted straight chain or branched chain alkyl group. Examples of the alkyl group having a carbon number of at least 1 and no greater than 3 include a methyl group, an ethyl group, a propyl group, and an isopropyl group.

An alkoxy group having a carbon number of at least 1 and no greater than 8 as used herein refers to an unsubstituted straight chain or branched chain alkoxy group. Examples of the alkoxy group having a carbon number of at least 1 and no greater than 8 include a methoxy group, an ethoxy group, an n-propoxy group, an isopropoxy group, an n-butoxy group, an s-butoxy group, a t-butoxy group, a pentyloxy group, an isopentyloxy group, a neopentyloxy group, a hexyloxy group, a heptyloxy group, and an octyloxy group.

An alkoxy group having a carbon number of at least 1 and no greater than 4 as used herein refers to an unsubstituted straight chain or branched chain alkoxy group. Examples of the alkoxy group having a carbon number of at least 1 and no greater than 4 include a methoxy group, an ethoxy group, an n-propoxy group, an isopropoxy group, an n-butoxy group, an s-butoxy group, and a t-butoxy group.

A cycloalkane having a carbon number of at least 5 and no greater than 7 as used herein is for example an unsubstituted cycloalkane having a carbon number of at least 5 and no greater than 7. Examples of the cycloalkane having a carbon number of at least 5 and no greater than 7 include cyclopentane, cyclohexane, and cycloheptane.

A cycloalkylidene group having a carbon number of at least 5 and no greater than 7 as used herein refers to an unsubstituted cycloalkylidene group. Examples of the cycloalkylidene group having a carbon number of at least 5 and no greater than 7 include a cyclopentylidene group, a cyclohexylidene group, and a cycloheptylidene group. The cycloalkylidene group having a carbon number of at least 5 and no greater than 7 is represented by a general formula shown below. In the general formula, d represents an integer of at least 1 and no greater than 3. Asterisks represent bonds. Preferably, d represents 2.

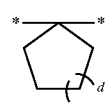

First Embodiment: Polyarylate Resin

A polyarylate resin according to a first embodiment of the present disclosure is represented by general formula (1) shown below. The polyarylate resin represented by general formula (1) is also referred to below as a polyarylate resin (1).

(1)

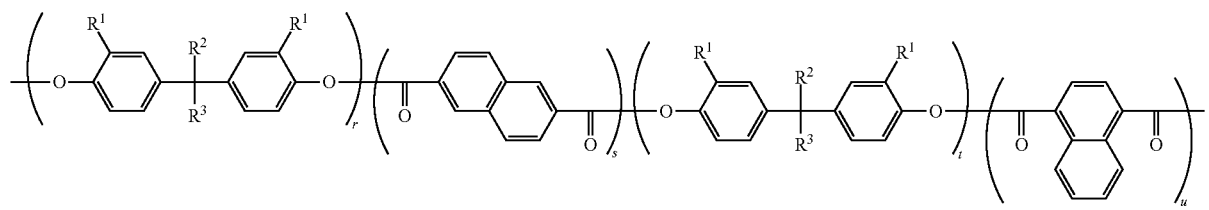

In general formula (1), $R^1$ represents a hydrogen atom or a methyl group. $R^2$ and $R^3$ each represent a hydrogen atom or an alkyl group having a carbon number of at least 1 and no greater than 4. $R^2$ and $R^3$ are not the same as one another. When $R^1$ represents a hydrogen atom, $R^2$ and $R^3$ are not bonded to one another. When $R^1$ represents a methyl group, $R^2$ and $R^3$ may be bonded to one another to form a ring. r and s each represent a number greater than or equal to 0 and less than or equal to 49. t and u each represent a number greater than or equal to 1 and less than or equal to 50. r+s+t+u=100. r+t=s+u. Each of the numbers represented by r, s, t, and u may be an integer or a decimal fraction.

Preferably, the alkyl group having a carbon number of at least 1 and no greater than 4 that may be represented by $R^2$ and $R^3$ in general formula (1) is a methyl group or an ethyl group. Preferably, $R^2$ and $R^3$ in general formula (1) each represent an alkyl group having a carbon number of at least 1 and no greater than 4, and more preferably a methyl group or an ethyl group. Still more preferably, one of $R^2$ and $R^3$ represents a methyl group, and the other of $R^2$ and $R^3$ represents an ethyl group.

In general formula (1), $R^2$ and $R^3$ may be bonded to one another to form a ring when $R^1$ represents a methyl group. The ring is for example a cycloalkylidene group having a carbon number of at least 5 and no greater than 7. Preferably, the ring is a cyclohexylidene group.

r and s may be different from one another. r and u may be different from one another. t and s may be different from one another. t and u may be different from one another.

The polyarylate resin (1) includes a repeating unit represented by general formula (1-5), a repeating unit represented by general formula (1-7), a repeating unit represented by chemical formula (1-6), and a repeating unit represented by chemical formula (1-8). The repeating units represented by general or chemical formulae (1-5), (1-7), (1-6), and (1-8) are also respectively referred to below as repeating units (1-5), (1-7), (1-6), and (1-8). The repeating unit (1-5) in the polyarylate resin (1) has a mole fraction of r/(r+t). The repeating unit (1-7) in the polyarylate resin (1) has a mole fraction of t/(r+t). The repeating unit (1-6) in the polyarylate resin (1) has a mole fraction of s/(s+u). The repeating unit (1-8) in the polyarylate resin (1) has a mole fraction of u/(s+u). r/(r+t) is a percentage (mole fraction) of the amount by mole of the repeating unit (1-5) relative to a sum of the amount by mole of the repeating unit (1-5) and the amount by mole of the repeating unit (1-7) in the polyarylate resin (1). s/(s+u) is a percentage (mole fraction) of the amount by mole of the repeating unit (1-6) relative to a sum of the amount by mole of the repeating unit (1-6) and the amount by mole of the repeating unit (1-8) in the polyarylate resin (1).

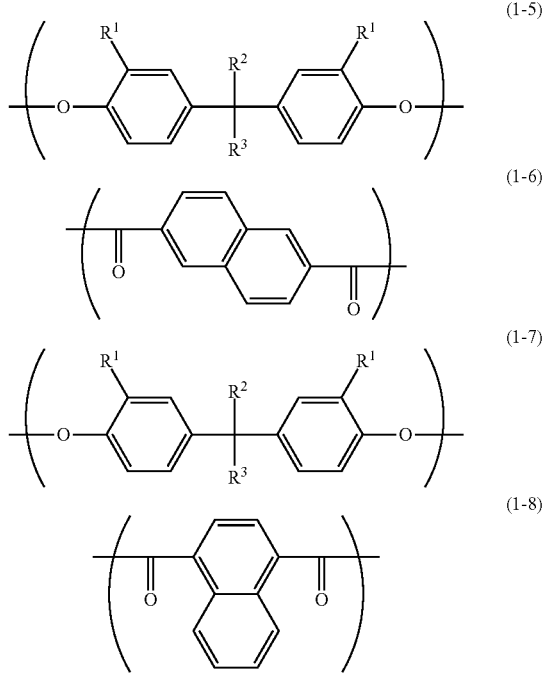

$R^1$, $R^2$, and $R^3$ in general formula (1-5) and general formula (1-6) are the same as defined for $R^1$, $R^2$, and $R^3$ in general formula (1).

When r and s represent 0, the polyarylate resin (1) does not have the repeating unit (1-5) or the repeating unit (1-6). When r and s represent 0, the polyarylate resin (1) has the repeating unit (1-7) and the repeating unit (1-8). When r represents a number greater than or equal to 1, the polyarylate resin (1) has the repeating unit (1-5) in addition to the repeating unit (1-7) and the repeating unit (1-8). When s represents a number greater than or equal to 1, the polyarylate resin (1) has the repeating unit (1-6) in addition to the repeating unit (1-7) and the repeating unit (1-8).

When r and s each represent a number greater than or equal to 1, the polyarylate resin (1) may have only the repeating units (1-5) to (1-8). Alternatively, the polyarylate resin (1) may have a repeating unit other than the repeating units (1-5) to (1-8). A ratio (mole fraction) of a sum of the amounts by mole of the repeating units (1-5) to (1-8) relative to the total amount by mole of all the repeating units included in the polyarylate resin (1) is preferably at least 0.80, more preferably at least 0.90, and still more preferably 1.00.

No particular limitations are placed on the sequence of the repeating units (1-5) to (1-8) in the polyarylate resin (1) so long as a repeating unit derived from an aromatic diol and a repeating unit derived from an aromatic dicarboxylic acid are adjacent to one another. The repeating unit derived from an aromatic diol is for example the repeating unit (1-5) and the repeating unit (1-7). The repeating unit derived from an aromatic dicarboxylic acid is for example the repeating unit (1-6) and the repeating unit (1-8). When the polyarylate resin (1) has only the repeating units (1-5) to (1-8), for example, the repeating unit (1-5) is adjacent to and bonded to the repeating unit (1-6) or the repeating unit (1-8). Likewise, for example, the repeating unit (1-7) is adjacent to and bonded to the repeating unit (1-6) or the repeating unit (1-8).

r and s in general formula (1) each represent a number greater than or equal to 0 and less than or equal to 49. t and u each represent a number greater than or equal to 1 and less than or equal to 50. r+s+t+u=100. r+t=s+u. Preferably, s/(s+u) is at least 0.30 and no greater than 0.70. As a result of s/(s+u) being at least 0.30 and no greater than 0.70, the polyarylate resin (1) included as a binder resin in a photosensitive layer of an electrophotographic photosensitive member, for example, easily improves abrasion resistance of the electrophotographic photosensitive member. An electrophotographic photosensitive member is also referred to below as a photosensitive member.

In terms of abrasion resistance of the photosensitive member, the binder resin preferably has a viscosity average molecular weight of at least 10,000, more preferably greater than 20,000, still more preferably greater than 30,000, and particularly preferably greater than 49,000. As a result of the binder resin having a viscosity average molecular weight of at least 10,000, the binder resin has increased abrasion resistance, and the photosensitive layer of the photosensitive member is resistant to abrasion. At the same time, the binder resin preferably has a viscosity average molecular weight of no greater than 80,000, and more preferably no greater than 64,000. As a result of the binder resin having a viscosity average molecular weight of no greater than 80,000, the binder resin is easily dissolved in a solvent during formation of the photosensitive layer of the photosensitive member, and therefore formation of the photosensitive layer tends to be easy.

No particular limitations are placed on the method for producing the binder resin so long as the method enables production of the polyarylate resin (1). Examples of production methods that can be employed include a method involving polycondensation of an aromatic dicarboxylic acid and an aromatic diol for forming repeating units of the polyarylate resin (1). No particular limitations are placed on the method for synthesizing the polyarylate resin (1). The polyarylate resin (1) may be synthesized according to a known synthesis method (specific examples include solution polymerization, melt polymerization, and interfacial polymerization).

The aromatic dicarboxylic acid has two carboxyl groups each bonded to an aromatic ring. The aromatic dicarboxylic acid is represented by chemical formula (1-9) or (1-10) (hereinafter, the aromatic dicarboxylic acids represented by chemical formulae (1-9) and (1-10) are also respectively referred to as aromatic dicarboxylic acids (1-9) and (1-10)).

(1-12) (hereinafter, the aromatic diols represented by general formulae (1-11) and (1-12) are also respectively referred to as aromatic diols (1-11) and (1-12)). $R^1$, $R^2$, and $R^3$ in general formulae (1-11) and (1-12) are respectively the same as defined for $R^1$, $R^2$, and $R^3$ in general formula (1).

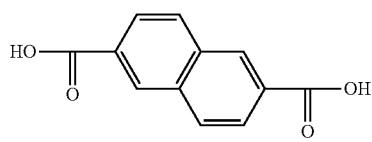

(1-9)

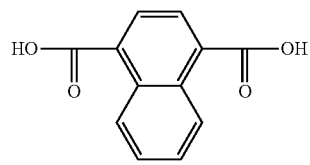

(1-10)

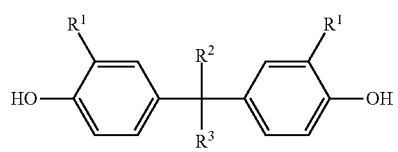

(1-11)

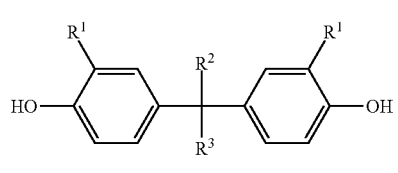

(1-12)

For synthesizing the polyarylate resin (1), a derivative of an aromatic dicarboxylic acid may be used instead of the aromatic dicarboxylic acid. Examples of derivatives of an aromatic dicarboxylic acid that can be used include alkanoyl halides (specific examples include dicarboxylic acid chloride), carboxylic acid esters (specific examples include dimethyl esters thereof), and dicarboxylic acid anhydrides.

For synthesizing the polyarylate resin (1), an aromatic dicarboxylic acid (specific examples include 4,4'-dicarboxydiphenyl ether, 4,4'-dicarboxybiphenyl, terephthalic acid, and isophthalic acid) other than the aromatic dicarboxylic acids (1-9) and (1-10) or a derivative of an aromatic dicarboxylic acid other than derivatives of the aromatic dicarboxylic acids (1-9) and (1-10) may be used.

The aromatic diol has two phenolic hydroxyl groups. The aromatic diol is represented by general formula (1-11) or Examples of aromatic diols that can be used include 1,1-bis(4-hydroxy-3-methylphenyl)cyclohexane, 2,2-bis(4-hydroxyphenyl)butane, 2,2-bis(4-hydroxy-3-methylphenyl)butane, and 1,1-bis(4-hydroxy-3-methylphenyl)ethane. For synthesizing the polyarylate resin (1), a derivative of an aromatic diol may be used instead of the aromatic diol. Examples of derivatives of an aromatic diol that can be used include esters (specific examples include diacetates).

For synthesizing the polyarylate resin (1), an aromatic diol other than the aromatic diols (1-11) and (1-12) or a derivative of an aromatic diol other than derivatives of the aromatic diols (1-11) and (1-12) may be used.

Examples of the polyarylate resin (1) include polyarylate resins represented by chemical formulae (R-1) to (R-7) (also respectively referred to below as polyarylate resins (R-1) to (R-7)).

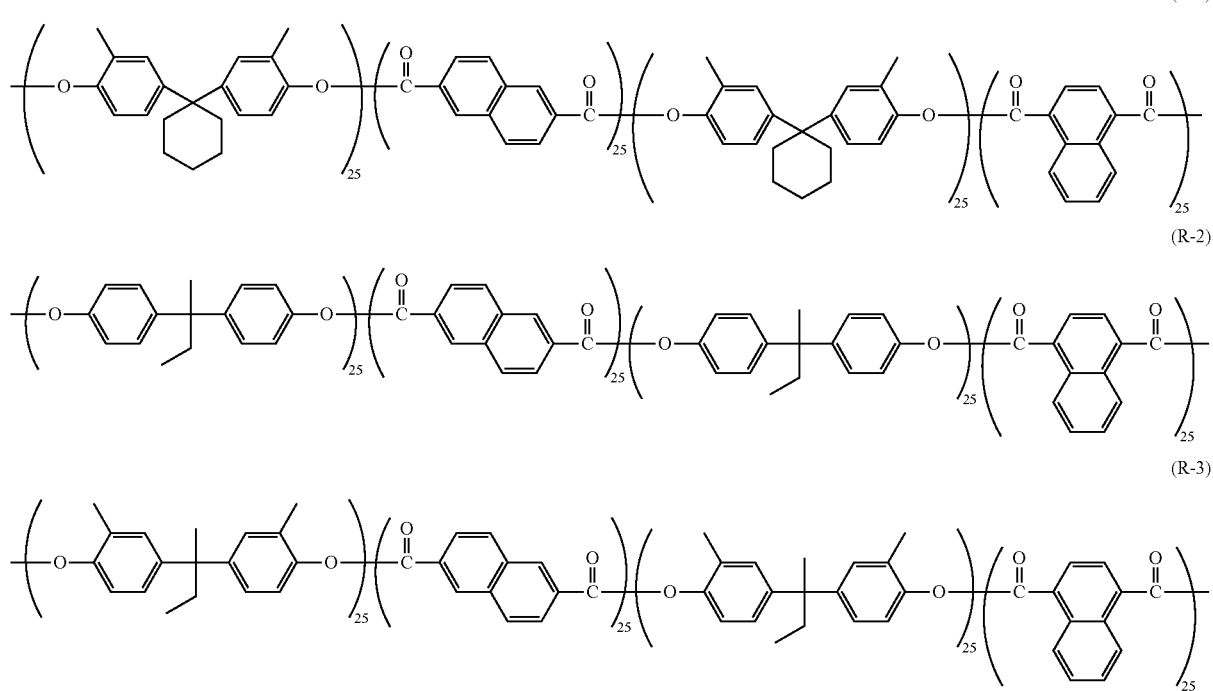

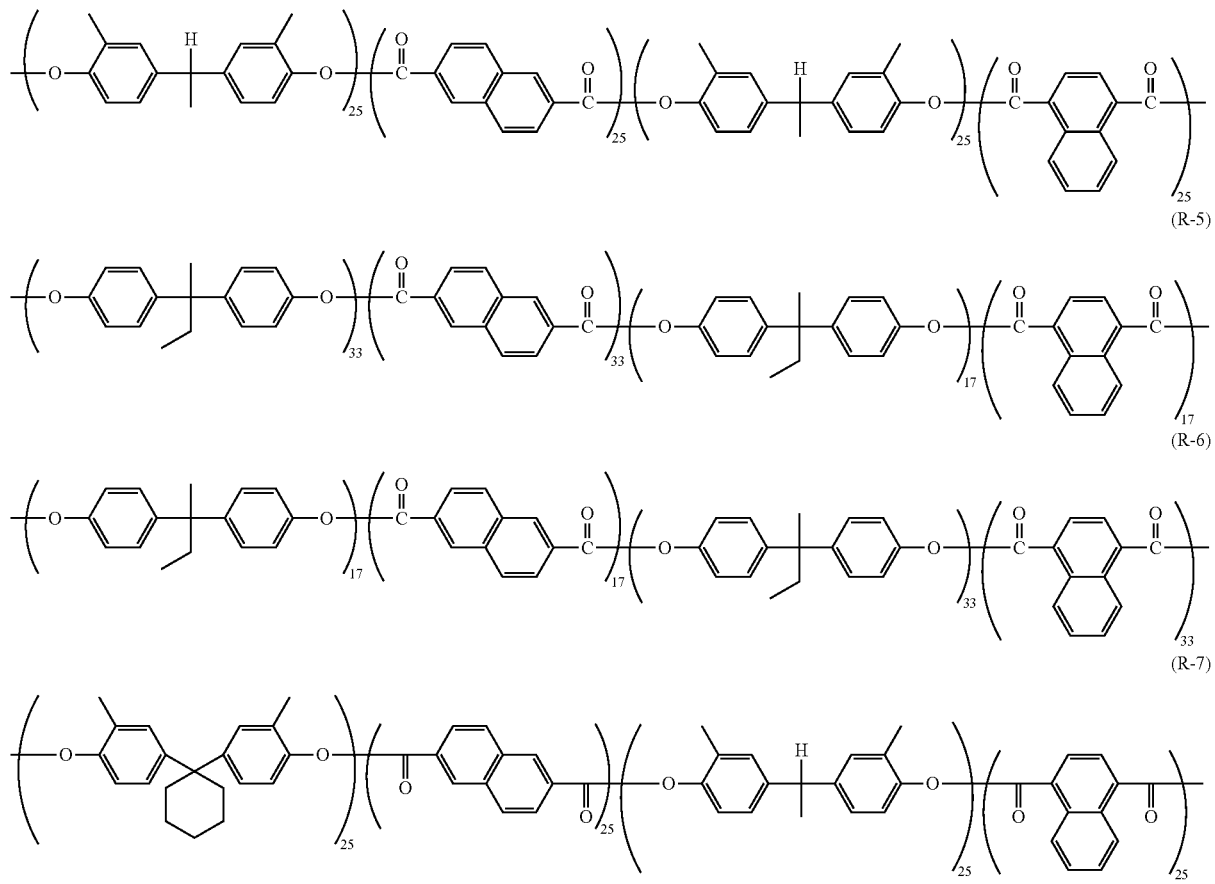

Through the above, the polyarylate resin (1) according to the first embodiment has been described. The polyarylate resin (1) according to the first embodiment included in a photosensitive layer of a photosensitive member can improve abrasion resistance of the photosensitive member.

Second Embodiment: Photosensitive Member

An electrophotographic photosensitive member according to a second embodiment of the present disclosure (also referred to below as a photosensitive member) includes a conductive substrate and a photosensitive layer. The photosensitive member is for example a multi-layer electrophotographic photosensitive member (also referred to below as a multi-layer photosensitive member) or a single-layer electrophotographic photosensitive member (also referred to below as a single-layer photosensitive member).

Figure 1B:
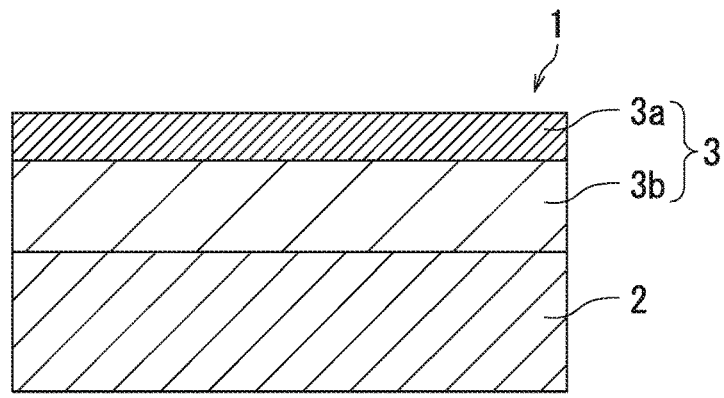
Figure 1C:
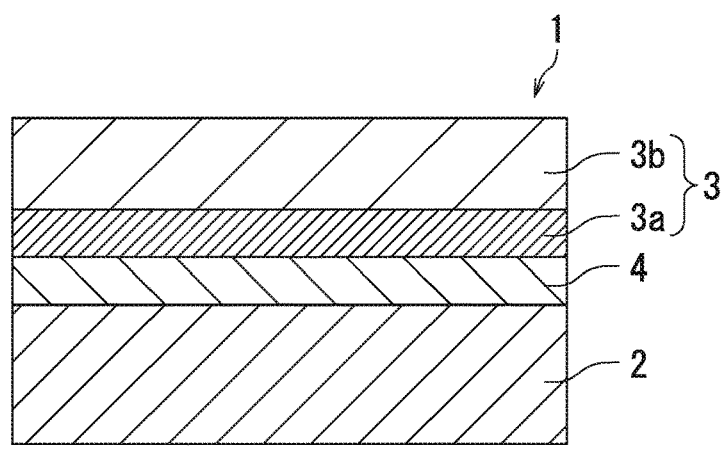

The photosensitive layer of the multi-layer photosensitive member includes a charge generating layer and a charge transport layer. The following describes a structure of a multi-layer photosensitive member 1 according to the second embodiment with reference to FIGS. 1A to 1C. FIGS. 1A to 1C are schematic cross-sectional views each illustrating the structure of the multi-layer photosensitive member 1. As illustrated in FIG. 1A, the multi-layer photosensitive member 1 includes a conductive substrate 2 and a photosensitive layer 3. The photosensitive layer 3 includes a charge generating layer 3a and a charge transport layer 3b. In the multi-layer photosensitive member 1, the charge generating layer 3a may be disposed on top of the conductive substrate 2 and the charge transport layer 3b may be disposed on top of the charge generating layer 3a as illustrated in FIG. 1A. Alternatively, in the multi-layer photosensitive member 1, the charge transport layer 3b may be disposed on top of the conductive substrate 2 and the charge generating layer 3a may be disposed on top of the charge transport layer 3b as illustrated in FIG. 1B. The charge transport layer 3b may be provided as an outermost layer of the multi-layer photosensitive member 1 as illustrated in FIG. 1A. The charge transport layer 3b may be a one-layer (single-layer) charge transport layer.

The photosensitive layer 3 may be disposed directly on the conductive substrate 2 as illustrated in FIG. 1A. Alternatively, the multi-layer photosensitive member 1 for example includes the conductive substrate 2, an intermediate layer (under layer) 4, and the photosensitive layer 3 as illustrated in FIG. 1C. The photosensitive layer 3 may be disposed indirectly on the conductive substrate 2 with the intermediate layer 4 therebetween as illustrated in FIG. 1C. The intermediate layer 4 may be disposed between the conductive substrate 2 and the charge generating layer 3a as illustrated in FIG. 1C. The intermediate layer 4 may for example be disposed between the charge generating layer 3a and the charge transport layer 3b. The charge generating layer 3a may be a single-layer or multi-layer charge generating layer.

The single-layer photosensitive member includes a single-layer photosensitive layer. The single-layer photosensitive member includes a conductive substrate and a photosensitive layer. The single-layer photosensitive member may include an intermediate layer. The photosensitive layer may be provided as an outermost layer of the single-layer photosensitive member.

The photosensitive member according to the second embodiment has excellent abrasion resistance. The reason for the above is thought to be as follows. The photosensitive member according to the second embodiment contains the polyarylate resin (1) as a binder resin. In general formula (1) representing the polyarylate resin (1), $R^2$ and $R^3$ are not the same as one another. When $R^1$ represents a hydrogen atom, $R^2$ and $R^3$ are not bonded to one another. When $R^1$ represents a methyl group, $R^2$ and $R^3$ may be bonded to one another to form a ring. The degree of molecular chain entanglement of the polyarylate resin (1) having such a structure tends not to decrease, and thus the degree of molecular packing thereof tends not to decrease. Furthermore, the polyarylate resin (1) having such a structure is highly soluble in a solvent. Accordingly, an application liquid for photosensitive layer formation is readily prepared. Consequently, the resulting photosensitive layer tends to have increased layer density. It is therefore thought that the photosensitive member according to the second embodiment is excellent in abrasion resistance.

The following describes elements (the conductive substrate, the photosensitive layer, and the intermediate layer) of the photosensitive member according to the second embodiment. The following further describes a method for producing the photosensitive member.

[1. Conductive Substrate]

No particular limitations are placed on the conductive substrate other than being a conductive substrate that can be used in the photosensitive member. At least a surface portion of the conductive substrate may be formed from a conductive material. For example, the conductive substrate is formed from a conductive material. For another example, the conductive substrate has a coat of a conductive material. Examples of conductive materials that can be used include aluminum, iron, copper, tin, platinum, silver, vanadium, molybdenum, chromium, cadmium, titanium, nickel, palladium, and indium. Any one of the conductive materials listed above may be used independently, or any two or more of the conductive materials listed above may be used in combination. Examples of combinations of conductive materials that can be used include alloys (more specifically, aluminum alloy, stainless steel, or brass).

Among the conductive materials listed above, aluminum or an aluminum alloy is preferable in terms of favorable charge mobility from the photosensitive layer to the conductive substrate.

The shape of the conductive substrate can be selected as appropriate in accordance with the structure of an image forming apparatus in which the conductive substrate is to be used. The conductive substrate is for example a sheet-shaped conductive substrate or a drum-shaped conductive substrate. The thickness of the conductive substrate can be selected as appropriate in accordance with the shape of the conductive substrate.

[2. Photosensitive Layer]

The photosensitive layer contains a charge generating material, a hole transport material, and a binder resin. The binder resin includes the polyarylate resin (1). The photosensitive layer may contain an additive. The photosensitive layer of the multi-layer photosensitive member includes a charge generating layer and a charge transport layer. The charge generating layer contains the charge generating material. The charge transport layer contains the hole transport material and the binder resin. No particular limitations are placed on thickness of the charge generating layer so long as the thickness thereof is sufficient to enable the charge generating layer to function as a charge generating layer. More specifically, the charge generating layer preferably has a thickness of at least 0.01 µm and no greater than 5 µm, and more preferably at least 0.1 µm and no greater than 3 µm. No particular limitations are placed on thickness of the charge transport layer so long as the thickness thereof is sufficient to enable the charge transport layer to function as a charge transport layer. More specifically, the charge transport layer preferably has a thickness of at least 2 µm and no greater than 100 µm, and more preferably at least 5 µm and no greater than 50 µm.

The photosensitive layer (single-layer photosensitive layer) of the single-layer photosensitive member contains a charge generating material, a hole transport material, and a binder resin. No particular limitations are placed on thickness of the photosensitive layer so long as the thickness thereof is sufficient to enable the photosensitive layer to function as a photosensitive layer. Specifically, the photosensitive layer may have a thickness of at least 5 µm and no greater than 100 µm. Preferably, the photosensitive layer has a thickness of at least 10 µm and no greater than 50 µm.

[2-1. Common Components]

The following describes the charge generating material, the hole transport material, and the binder resin. The following further describes additives.

[2-1-1. Charge Generating Material]

No particular limitations are placed on the charge generating material other than being a charge generating material that can be used in the photosensitive member. Examples of charge generating materials that can be used include phthalocyanine-based pigments, perylene-based pigments, bisazo pigments, dithioketopyrrolopyrrole pigments, metal-free naphthalocyanine pigments, metal naphthalocyanine pigments, squaraine pigments, tris-azo pigments, indigo pigments, azulenium pigments, cyanine pigments, powders of inorganic photoconductive materials such as selenium, selenium-tellurium, selenium-arsenic, cadmium sulfide, or amorphous silicon, pyrylium salts, anthanthrone-based pigments, triphenylmethane-based pigments, threne-based pigments, toluidine-based pigments, pyrazoline-based pigments, and quinacridone-based pigments. Examples of phthalocyanine-based pigments that can be used include pigments of phthalocyanine and pigments of phthalocyanine derivatives. Examples of phthalocyanine that can be used include metal-free phthalocyanine pigments (specific examples include X-form metal-free phthalocyanine (x-$H_2$Pc)). Examples of phthalocyanine derivatives that can be used include metal phthalocyanine pigments (specific examples include titanyl phthalocyanine and V-form hydroxygallium phthalocyanine). No particular limitations are placed on the crystal structure of the phthalocyanine-based pigments, and phthalocyanine-based pigments having various different crystal structures may be used. The phthalocyanine-based pigment for example has an α-form, a β-form, or a Y-form crystal structure. The photosensitive layer (the charge generating layer or the single-layer photosensitive layer) may contain only one charge generating material or may contain two or more charge generating materials. Of the charge generating materials listed above, phthalocyanine-based pigments are preferable, metal phthalocyanine pigments are more preferable, and Y-form titanyl phthalocyanine is still more preferable.

Any one charge generating material or a combination of any two or more charge generating materials that is absorptive with respect to light in a desired wavelength region may be used. In a digital optical system image forming apparatus, for example, a photosensitive member that is sensitive to a range of wavelengths that are greater than or equal to 700 nm is preferably used. The digital optical system image forming apparatus may for example be a laser beam printer or facsimile machine in which a light source such as a semiconductor laser is used. Accordingly, for example, a phthalocyanine-based pigment is preferable, and Y-form titanyl phthalocyanine (Y-TiOPc) is more preferable. The Y-form titanyl phthalocyanine may exhibit a peak at a Bragg angle $2\theta \pm 0.2° = 27.2°$ in a CuKα characteristic X-ray diffraction spectrum.

A photosensitive member included in an image forming apparatus that uses a short-wavelength laser light source preferably contains an anthanthrone-based pigment or a perylene-based pigment as a charge generating material. The short-wavelength laser light source for example has an approximate wavelength of at least 350 mu and no greater than 550 nm.

The charge generating material is for example any of phthalocyanine-based pigments represented by chemical formulae (CGM-1) to (CGM-4) (also respectively referred to below as charge generating materials (CGM-1) to (CGM-4)).

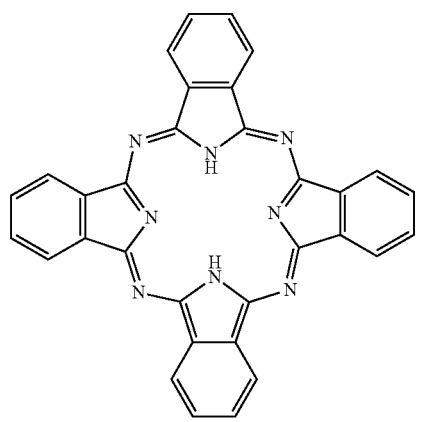
(CGM-1)

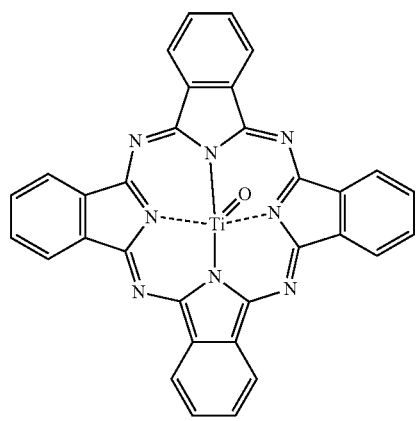
(CGM-2)

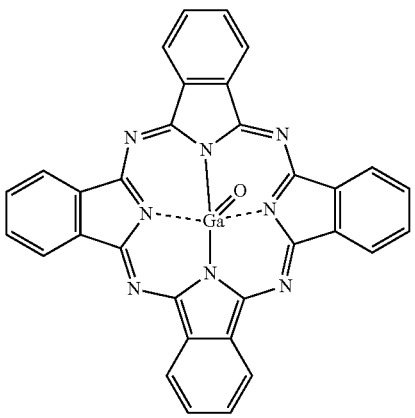
(CGM-3)

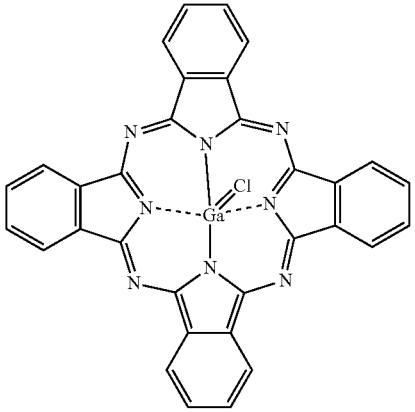
(CGM-4)

The charge generating material is preferably contained in an amount of at least 5 parts by mass and no greater than 1,000 parts by mass relative to 100 parts by mass of a binder resin for the charge generating layer (also referred to below as a base resin), and more preferably in an amount of at least 30 parts by mass and no greater than 500 parts by mass.

[2-1-2. Hole Transport Material]

Examples of hole transport materials that can be used include triarylamine derivatives, diamine derivatives (specific examples include N,N,N',N'-tetraphenylphenylenediamine derivatives, N,N,N',N'-tetraphenylnaphtylenediamine derivatives, and N,N,N',N'-tetraphenylphenanthrylenediamine derivatives), oxadiazole-based compounds (specific examples include 2,5-di(4-methylaminophenyl)-1,3,4-oxadiazole), styryl-based compounds (specific examples include 9-(4-diethylaminostyryl)anthracene), carbazole-based compounds (specific examples include polyvinyl carbazole), organic polysilane compounds, pyrazoline-based compounds (specific examples include 1-phenyl-3-(p-dimethylaminophenyl)pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. Of the hole transport materials listed above, compounds represented by general formulae (2), (3), and (4) are preferable. In terms of further improving abrasion resistance of the photosensitive member, the hole transport material preferably includes the compound represented by general formula (2), (3), or (4), and more preferably includes the compound represented by general formula (2) or (3). Still more preferably, in terms of improving electrical characteristics of the photosensitive member in addition to abrasion resistance of the photosensitive member, the hole transport material includes the compound represented by general formula (4).

In general formula (2), $Q^1$ represents a hydrogen atom, an alkyl group having a carbon number of at least 1 and no greater than 8, an alkoxy group having a carbon number of at least 1 and no greater than 8, or a phenyl group optionally substituted with an alkyl group having a carbon number of at least 1 and no greater than 8. $Q^2$ represents an alkyl group having a carbon number of at least 1 and no greater than 8,

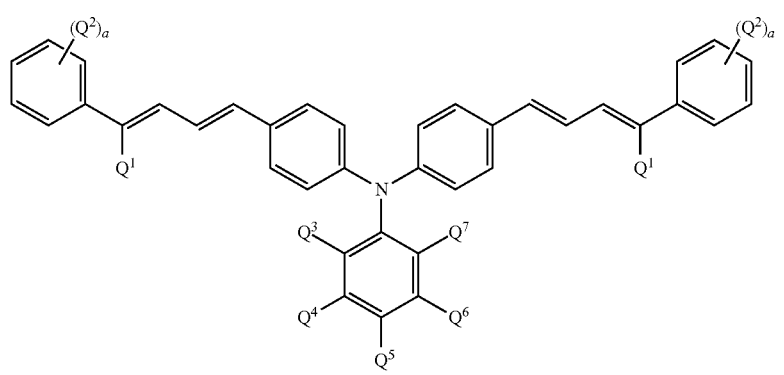

(2)

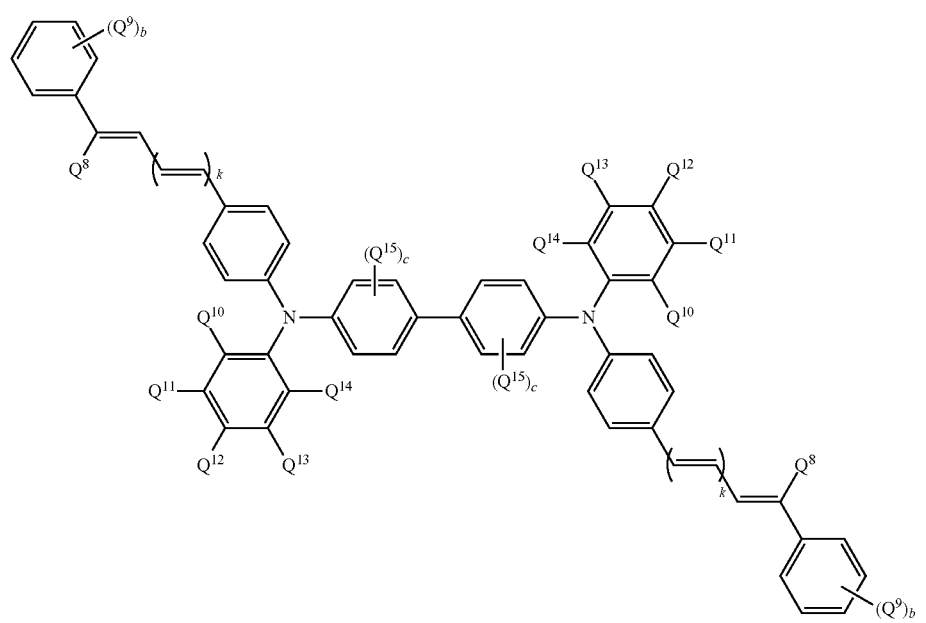

(3)

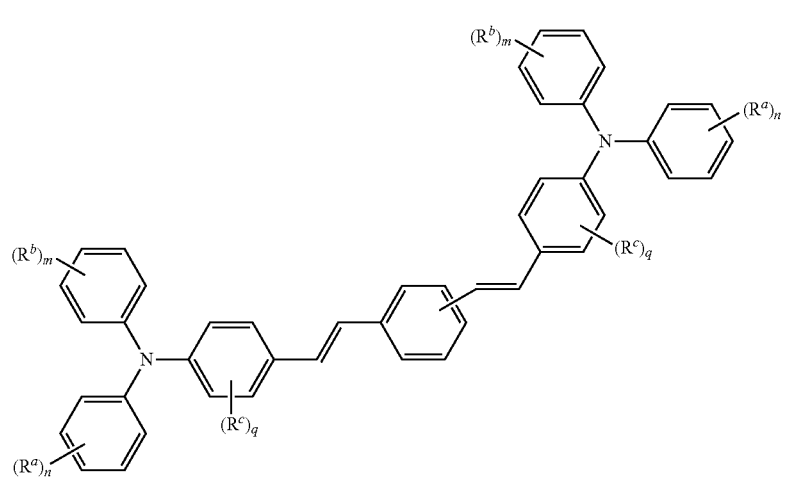

(4)

an alkoxy group having a carbon number of at least 1 and no greater than 8, or a phenyl group. $Q^3$, $Q^4$, $Q^5$, $Q^6$, and $Q^7$ each represent, independently of one another, a hydrogen atom, an alkyl group having a carbon number of at least 1 and no greater than 8, an alkoxy group having a carbon number of at least 1 and no greater than 8, or a phenyl group. Adjacent two members among $Q^3$, $Q^4$, $Q^5$, $Q^6$, and $Q^7$ are optionally bonded to one another to form a ring. a represents an integer of at least 0 and no greater than 5. When a represents an integer of at least 2 and no greater than 5, chemical groups $Q^2$ bonded to the same phenyl group may be the same as or different from one another.

In general formula (3), $Q^8$, $Q^{10}$, $Q^{11}$, $Q^{12}$, $Q^{13}$, and $Q^{14}$ each represent, independently of one another, a hydrogen atom, an alkyl group having a carbon number of at least 1 and no greater than 8, an alkoxy group having a carbon number of at least 1 and no greater than 8, or a phenyl group. $Q^9$ and $Q^{15}$ each represent, independently of one another, an alkyl group having a carbon number of at least 1 and no greater than 8, an alkoxy group having a carbon number of at least 1 and no greater than 8, or a phenyl group. b represents an integer of at least 0 and no greater than 5. When b represents an integer of at least 2 and no greater than 5, chemical groups $Q^9$ bonded to the same phenyl group may be the same as or different from one another. c represents an integer of at least 0 and no greater than 4. When c represents an integer of at least 2 and no greater than 4, chemical groups $Q^{15}$ bonded to the same phenyl group may be the same as or different from one another. k represents 0 or 1.

In general formula (4), $R^a$, $R^b$, and $R^c$ each represent, independently of one another, an alkyl group having a carbon number of at least 1 and no greater than 8, a phenyl group, or an alkoxy group having a carbon number of at least 1 and no greater than 8. q represents an integer of at least 0 and no greater than 4. When q represents an integer of at least 2 and no greater than 4, chemical groups $R^c$ bonded to the same phenyl group may be the same as or different from one another. m and n each represent, independently of one another, an integer of at least 0 and no greater than 5. When m represents an integer of at least 2 and no greater than 5, chemical groups $R^b$ bonded to the same phenyl group may be the same as or different from one another. When n represents an integer of at least 2 and no greater than 5, chemical groups $R^a$ bonded to the same phenyl group may be the same as or different from one another.

In general formula (2), $Q^1$ is preferably a phenyl group substituted with an alkyl group having a carbon number of at least 1 and no greater than 8, and more preferably a phenyl group substituted with a methyl group.

In general formula (2), the alkyl group having a carbon number of at least 1 and no greater than 8 that may be represented by $Q^2$ is preferably an alkyl group having a carbon number of at least 1 and no greater than 6, more preferably an alkyl group having a carbon number of at least 1 and no greater than 4, and still more preferably a methyl group. Preferably, a represents 0 or 1.

In general formula (2), the alkyl group having a carbon number of at least 1 and no greater than 8 that may be represented by $Q^3$ to $Q^7$ is preferably an alkyl group having a carbon number of at least 1 and no greater than 4, and more preferably a methyl group, an ethyl group, or an n-butyl group. In general formula (2), the alkoxy group having a carbon number of at least 1 and no greater than 8 that may be represented by $Q^3$ to $Q^7$ is preferably an alkoxy group having a carbon number of at least 1 and no greater than 4, and more preferably a methoxy group. In general formula (2), $Q^3$ to $Q^7$ each preferably represent, independently of one another, a hydrogen atom, an alkyl group having a carbon number of at least 1 and no greater than 8, or an alkoxy group having a carbon number of at least 1 and no greater than 8, and more preferably a hydrogen atom, an alkyl group having a carbon number of at least 1 and no greater than 4, or an alkoxy group having a carbon number of at least 1 and no greater than 4.

In general formula (2), adjacent two members among $Q^3$ to $Q^7$ are optionally bonded to one another to form a ring (more specifically, a benzene ring or a cycloalkane having a carbon number of at least 5 and no greater than 7). For example, adjacent $Q^6$ and $Q^7$ among $Q^3$ to $Q^7$ may be bonded to one another to form a benzene ring or a cycloalkane having a carbon number of at least 5 and no greater than 7. When adjacent two members among $Q^3$ to $Q^7$ are bonded to one another to form a benzene ring, the benzene ring forms a bicyclic fused ring group (naphthyl group) through fusion with the phenyl group bonded to $Q^3$ to $Q^7$. When adjacent two members among $Q^3$ to $Q^7$ are bonded to one another to form a cycloalkane having a carbon number of at least 5 and no greater than 7, the cycloalkane having a carbon number of at least 5 and no greater than 7 forms a bicyclic fused ring group through fusion with the phenyl group bonded to $Q^3$ to $Q^7$. In such a case, the site of fusion between the phenyl group and the cycloalkane having a carbon number of at least 5 and no greater than 7 may include a double bond. Two adjacent members among $Q^3$ to $Q^7$ preferably form a cycloalkane having a carbon number of at least 5 and no greater than 7, and more preferably form cyclohexane.

In general formula (2), $Q^1$ preferably represents a hydrogen atom or a phenyl group substituted with an alkyl group having a carbon number of at least 1 and no greater than 8. Preferably, $Q^2$ represents an alkyl group having a carbon number of at least 1 and no greater than 8. Preferably, $Q^3$ to $Q^7$ each represent, independently of one another, a hydrogen atom, an alkyl group having a carbon number of at least 1 and no greater than 8, or an alkoxy group having a carbon number of at least 1 and no greater than 8. Preferably, adjacent two members among $Q^3$ to $Q^7$ are bonded to one another to form a ring. Preferably, a represents 0 or 1.

In general formula (3), the alkyl group having a carbon number of at least 1 and no greater than 8 that may be represented by $Q^8$ and $Q^{10}$ to $Q^{14}$ is preferably an alkyl group having a carbon number of at least 1 and no greater than 4, and more preferably a methyl group or an ethyl group. In general formula (3), $Q^8$ and $Q^{10}$ to $Q^{14}$ each preferably represent, independently of one another, a hydrogen atom, an alkyl group having a carbon number of at least 1 and no greater than 4, or a phenyl group. In general formula (3), b and c each preferably represent 0. k represents 0 or 1.

In general formula (4), the alkyl group having a carbon number of at least 1 and no greater than 8 that may be represented by $R_a$ and $R_b$ is preferably an alkyl group having a carbon number of at least 1 and no greater than 4, and more preferably a methyl group or an ethyl group. m and n each represent, independently of one another, an integer of at least 0 and no greater than 2. Preferably, q represents 0.

Examples of compounds represented by general formula (2) include compounds represented by chemical formulae (HTM-1) to (HTM-4) (also respectively referred to below as hole transport materials (HTM-1) to (HTM-4)). Examples of compounds represented by general formula (3) include compounds represented by chemical formulae (HTM-5) to (HTM-7) (also respectively referred to below as hole transport materials (HTM-5) to (HTM-7)). Examples of compounds represented by general formula (4) include compounds represented by chemical formulae (HTM-8) and (HTM-9) (also respectively referred to below as hole transport materials (HTM-8) and (HTM-9)).
(HTM-1)
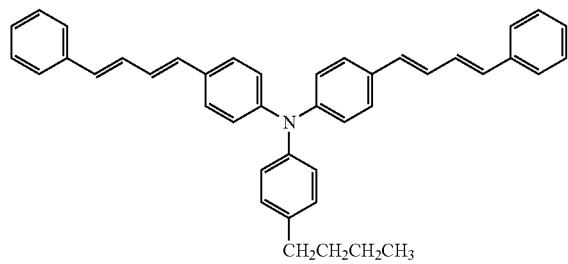
(HTM-2)
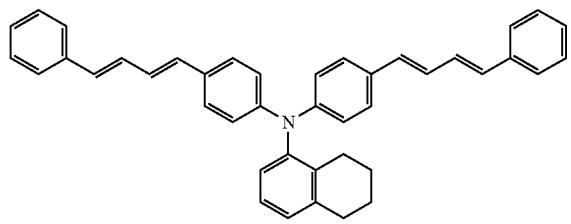
(HTM-3)
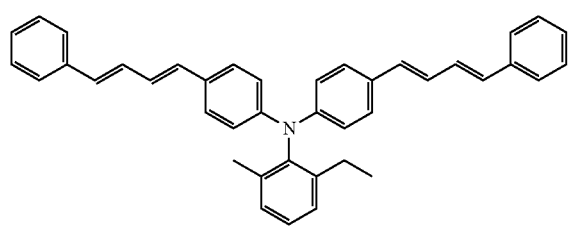
(HTM-4)
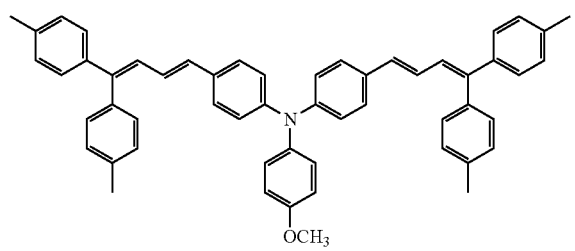
(HTM-5)
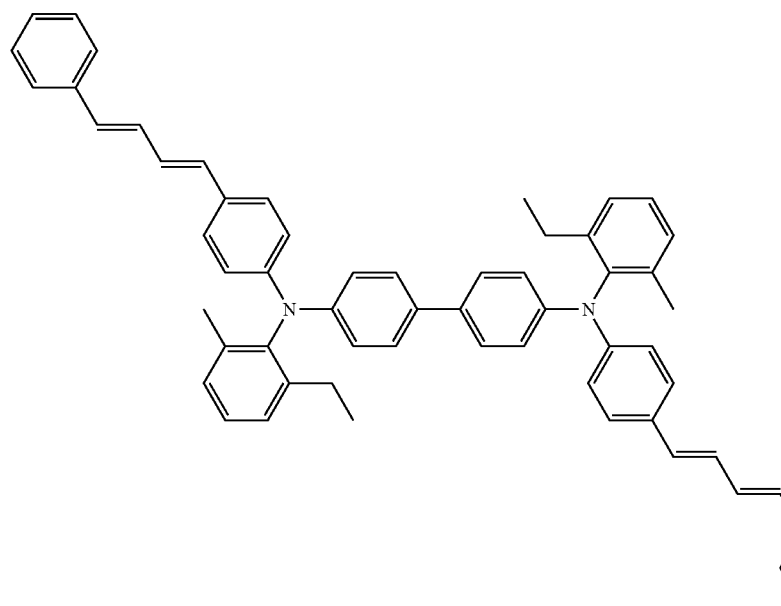
(HTM-6)
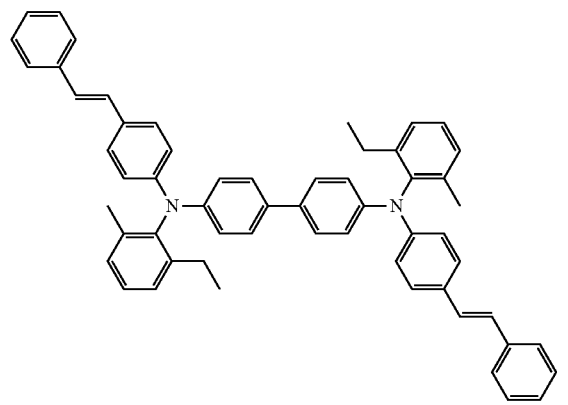
(HTM-7)
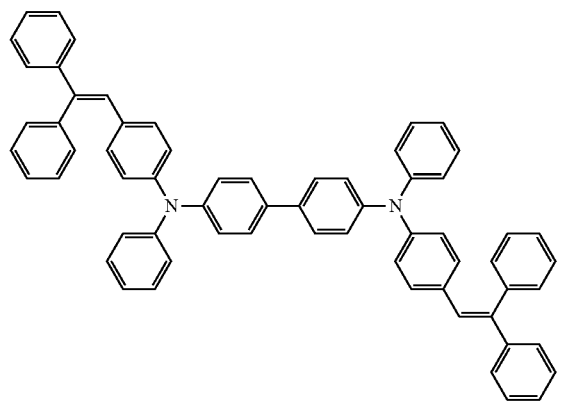

(HTM-8)

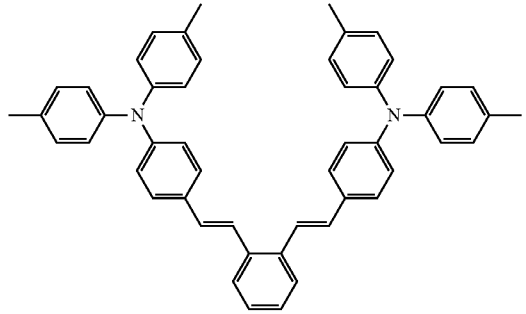

-continued (HTM-9)

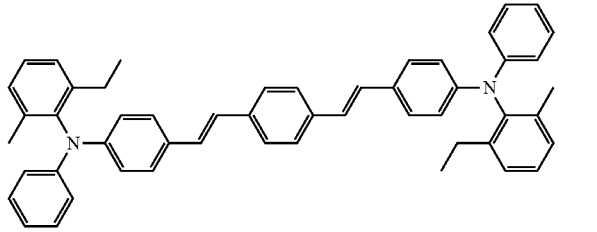

The photosensitive layer (for example, the charge transport layer or the single-layer photosensitive layer) may contain only one of the compounds represented by general formulae (2), (3), and (4). The photosensitive layer (for example, the charge transport layer or the single-layer photosensitive layer) may contain two or more of the compounds represented by general formulae (2), (3), and (4).

The photosensitive layer (for example, the charge transport layer or the single-layer photosensitive layer) may contain only one of the compounds (HTM-1) to (HTM-9). The photosensitive layer (for example, the charge transport layer or the single-layer photosensitive layer) may contain two or more of the compounds (HTM-1) to (HTM-9).

The hole transport material is preferably contained in the multi-layer photosensitive member in an amount of at least 10 parts by mass and no greater than 200 parts by mass relative to 100 parts by mass of the binder resin, and more preferably in an amount of at least 20 parts by mass and no greater than 100 parts by mass.

[2-1-3. Binder Resin]

The binder resin is used in the charge transport layer of the multi-layer photosensitive member or in the photosensitive layer of the single-layer photosensitive member. The binder resin includes the polyarylate resin (1). As a result of containing the polyarylate resin (1), the photosensitive member can have improved abrasion resistance.

The photosensitive layer (for example, the charge transport layer or the single-layer photosensitive layer) may contain only one polyarylate resin (1) as the binder resin. The photosensitive layer (for example, the charge transport layer or the single-layer photosensitive layer) may contain two or more polyarylate resins (1) as the binder resin. The photosensitive layer (for example, the charge transport layer or the single-layer photosensitive layer) may contain only the polyarylate resin (1) as the binder resin. The photosensitive layer (for example, the charge transport layer or the single-layer photosensitive layer) may contain, as the binder resin, the polyarylate resin (1) and an optional resin that is not the polyarylate resin (1). Examples of optional resins that can be used include thermoplastic resins, thermosetting resins, and photocurable resins. Examples of thermoplastic resins that can be used include polyarylate resins other than the polyarylate resin (1), polycarbonate resins, styrene-based resins, styrene-butadiene copolymers, styrene-acrylonitrile copolymers, styrene-maleic acid copolymers, styrene-acrylic acid copolymers, acrylic copolymers, polyethylene resins, ethylene-vinyl acetate copolymers, chlorinated polyethylene resins, polyvinyl chloride resins, polypropylene resins, ionomers, vinyl chloride-vinyl acetate copolymers, polyester resins, alkyd resins, polyamide resins, polyurethane resins, polysulfone resins, diallyl phthalate resins, ketone resins, polyvinyl butyral resins, and polyether resins. Examples of thermosetting resins that can be used include silicone resins, epoxy resins, phenolic resins, urea resins, melamine resins, and other crosslinkable thermosetting resins. Examples of photocurable resins that can be used include epoxy-acrylic acid-based resins and urethane-acrylic acid-based copolymers. Any one of the resins listed above may be used independently, or any two or more of the resins listed above may be used in combination. The polyarylate resin (1) is preferably contained in an amount of at least 80 parts by mass relative to 100 parts by mass of the binder resin, more preferably in an amount of at least 90 parts by mass, and still more preferably in an amount of 100 parts by mass.

In the second embodiment, the binder resin content is preferably at least 40% by mass and no greater than 60% by mass of the total mass of all the components contained in the charge transport layer (for example, the hole transport material, the binder resin, and the additive).

[2-1-4. Additive]

Various additives may be contained in one or more of the charge generating layer, the charge transport layer, the photosensitive layer of the single-layer photosensitive member, and the intermediate layer, so long as such additives do not adversely affect electrophotographic properties of the photosensitive member. Examples of additives that can be used include antidegradants (specific examples include antioxidants, radical scavengers, quenchers, and ultraviolet absorbing agents), softeners, surface modifiers, extenders, thickeners, dispersion stabilizers, waxes, electron acceptor compounds, donors, surfactants, and leveling agents.

Examples of softeners that can be used include meta-terphenyl. Examples of leveling agents that can be used include silicone oil (specific examples include dimethyl silicone oil).

The softener is preferably contained in the charge transport layer in an amount of at least 0.5 parts by mass and no greater than 50 parts by mass relative to 100 parts by mass of the binder resin, and more preferably in an amount of at least 1 part by mass and no greater than 10 parts by mass.

[2-1-5. Combination of Materials]

Preferably, the binder resin and the hole transport material are any one of combinations described below. More preferably, the binder resin and the hole transport material are any one of the combinations described below, and the charge generating material is Y-form titanyl phthalocyanine. Still more preferably, the binder resin and the hole transport material are any one of the combinations described below, the charge generating material is Y-form titanyl phthalocyanine, and the additives are dimethyl silicone oil and meta-terphenyl.

The binder resin is the polyarylate resin (R-1), and the hole transport material is any one of the compounds (HTM-1), (HTM-2), (HTM-3), (HTM-4), (HTM-5), (HTM-6), (HTM-7), (HTM-8), and (HTM-9);

the binder resin is the polyarylate resin (R-2), and the hole transport material is any one of the compounds (HTM-1), (HTM-2), (HTM-3), (HTM-4), (HTM-5), (HTM-6), (HTM-7), (HTM-8), and (HTM-9);

the binder resin is the polyarylate resin (R-3), and the hole transport material is any one of the compounds (HTM-1), (HTM-2), (HTM-3), (HTM-4), (HTM-5), (HTM-6), (HTM-7), (HTM-8), and (HTM-9);

the binder resin is the polyarylate resin (R-4), and the hole transport material is any one of the compounds (HTM-1), (HTM-2), (HTM-3), (HTM-4), (HTM-5), (HTM-6), (HTM-7), (HTM-8), and (HTM-9);

the binder resin is the polyarylate resin (R-5), and the hole transport material is any one of the compounds (HTM-1), (HTM-2), (HTM-3), (HTM-4), (HTM-5), (HTM-6), (HTM-7), (HTM-8), and (HTM-9);

the binder resin is the polyarylate resin (R-6), and the hole transport material is any one of the compounds (HTM-1), (HTM-2), (HTM-3), (HTM-4), (HTM-5), (HTM-6), (HTM-7), (HTM-8), and (HTM-9); or the binder resin is the polyarylate resin (R-7), and the hole transport material is any one of the compounds (HTM-1), (HTM-2), (HTM-3), (HTM-4), (HTM-5), (HTM-6), (HTM-7), (HTM-8), and (HTM-9).

[2-2. Non-Common Components]

The charge generating layer of the multi-layer photosensitive member may contain a binder resin for the charge generating layer (also referred to below as a base resin). No particular limitations are placed on the base resin other than being a base resin that can be used in the photosensitive member. Examples of base resins that can be used include thermoplastic resins, thermosetting resins, and photocurable resins. Examples of thermoplastic resins that can be used include styrene-based resins, styrene-butadiene copolymers, styrene-acrylonitrile copolymers, styrene-maleic acid copolymers, styrene-acrylic acid-based copolymers, acrylic copolymers, polyethylene resins, ethylene-vinyl acetate copolymers, chlorinated polyethylene resins, polyvinyl chloride resins, polypropylene resins, ionomers, vinyl chloride-vinyl acetate copolymers, alkyd resins, polyamide resins, urethane resins, polycarbonate resins, polyarylate resins, polysulfone resins, diallyl phthalate resins, ketone resins, polyvinyl butyral resins, polyether resins, and polyester resins. Examples of thermosetting resins that can be used include silicone resins, epoxy resins, phenolic resins, urea resins, melamine resins, and other crosslinkable thermosetting resins. Examples of photocurable resins that can be used include epoxy-acrylic acid-based resins and urethane-acrylic acid-based resins. Any one of the base resins listed above may be used independently, or any two or more of the base resins listed above may be used in combination.

Although resins that are listed as examples of the binder resin described earlier are also listed as examples of the base resin, a resin that is different from the binder resin is normally selected as the base resin in the same multi-layer photosensitive member for the following reason. In production of the multi-layer photosensitive member, the charge generating layer and the charge transport layer are normally formed in the stated order, and thus an application liquid for charge transport layer formation is normally coated onto the charge generating layer. The charge generating layer is preferably insoluble in a solvent of the application liquid for charge transport layer formation during the formation of the charge transport layer. Therefore, a resin that is different from the binder resin is normally selected as the base resin in the same multi-layer photosensitive member.

[3. Intermediate Layer]

The photosensitive member according to the second embodiment may optionally include the intermediate layer (for example, an underlayer). The intermediate layer for example contains inorganic particles and a resin (intermediate layer resin). Provision of the intermediate layer can facilitate flow of current generated when the photosensitive member is exposed to light and inhibit increasing resistance, while also maintaining insulation to a sufficient degree so as to inhibit occurrence of leakage current.

Examples of inorganic particles that can be used include particles of metals (specific examples include aluminum, iron, and copper), metal oxides (specific examples include titanium oxide, alumina, zirconium oxide, tin oxide, and zinc oxide), and non-metal oxides (specific examples include silica). Any one type of the inorganic particles listed above may be used independently, or any two or more types of the inorganic particles listed above may be used in combination.

No particular limitations are placed on the intermediate layer resin other than being a resin that can be used to form the intermediate layer.

[4. Production Method of Photosensitive Member]

The following describes a method for producing the photosensitive member. The production method of the photosensitive member for example includes a photosensitive layer formation process.

[4-1. Production Method of Multi-Layer Photosensitive Member]

The photosensitive layer formation process in the production method of the multi-layer photosensitive member has a charge generating layer formation process and a charge transport layer formation process. In the charge generating layer formation process, first, an application liquid for formation of the charge generating layer (also referred to below as an application liquid for charge generating layer formation) is prepared. The application liquid for charge generating layer formation is applied onto the conductive substrate to form a film. Next, the film is dried by an appropriate method to remove at least a portion of a solvent in the film. Thus, the charge generating layer is formed. The application liquid for charge generating layer formation for example contains a charge generating material, a base resin, and a solvent. The application liquid for charge generating layer formation is prepared by dissolving or dispersing the charge generating material and the base resin in the solvent. Additives may optionally be added to the application liquid for charge generating layer formation.

In the charge transport layer formation process, first, an application liquid for formation of the charge transport layer (also referred to below as an application liquid for charge transport layer formation) is prepared. The application liquid for charge transport layer formation is applied onto the charge generating layer to form a film. Next, the film is dried by an appropriate method to remove at least a portion of a solvent in the film. Thus, the charge transport layer is formed. The application liquid for charge transport layer formation contains a hole transport material, the polyarylate resin (1) as a binder resin, and a solvent. The application liquid for charge transport layer formation can be prepared by dissolving or dispersing the hole transport material and the polyarylate resin (1) in the solvent. Additives may optionally be added to the application liquid for charge transport layer formation.

[4-2. Production Method of Single-Layer Photosensitive Member]

In the photosensitive layer formation process of the production method of the single-layer photosensitive member, an application liquid for formation of the photosensitive layer (also referred to below as an application liquid for photosensitive layer formation) is prepared. The application liquid for photosensitive layer formation is applied onto the conductive substrate to form a film. Next, the film is dried by an appropriate method to remove at least a portion of a solvent in the film. Thus, the photosensitive layer is formed. The application liquid for photosensitive layer formation for example contains a charge generating material, a hole transport material, the polyarylate resin (1) as a binder resin, and a solvent. The application liquid for photosensitive layer formation is prepared by dissolving or dispersing the charge generating material, the hole transport material, and the polyarylate resin (1) in the solvent. Additives may optionally be added to the application liquid for photosensitive layer formation.

The following describes the photosensitive layer formation process in detail. No particular laminations are placed on the solvents contained in the application liquid for charge generating layer formation, the application liquid for charge transport layer formation, and the application liquid for photosensitive layer formation (these three application liquids may be also referred to below as application liquids) other than that components of the application liquids should be soluble or dispersible in the solvents. Examples of solvents that can be used include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, and diethylene glycol dimethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used independently, or any two or more of the solvents listed above may be used in combination. Of the solvents listed above, a non-halogenated solvent is preferably used.

Preferably, the solvent contained in the application liquid for charge transport layer formation and the solvent contained in the application liquid for charge generating layer formation are different for the following reason. In production of the multi-layer photosensitive member, the charge generating layer and the charge transport layer are normally formed in the stated order, and thus the application liquid for charge transport layer formation is normally coated onto the charge generating layer. During formation of the charge transport layer, the charge generating layer is desirably insoluble in the solvent contained in the application liquid for charge transport layer formation.

Each application liquid is prepared by mixing the components to disperse the components in the solvent. Mixing or dispersion can for example be performed using a bead mill, a roll mill, a ball mill, an attritor, a paint shaker, or an ultrasonic disperser.

The application liquids may for example include a surfactant or a leveling agent in order to improve dispersibility of the components or improve surface flatness of the formed layers.

No particular limitations are placed on the method by which the application liquid is applied so long as the method enables uniform application of the application liquid. Examples of application methods that can be used include dip coating, spray coating, spin coating, and bar coating.

No particular limitations are placed on the method by which at least a portion of the solvent in each application liquid is removed other than being a method that enables evaporation of the solvent in the application liquid. Examples of methods that can be used to remove the solvent include heating, pressure reduction, and a combination of heating and pressure reduction. One specific example of a method involves heat treatment (specific examples include hot-air drying) using a high-temperature dryer or a reduced pressure dryer. The heat treatment is for example performed for at least 3 minutes and no greater than 120 minutes at a temperature of at least 40° C. and no greater than 150° C.

Note that the production method of the photosensitive member may further include a process of forming the intermediate layer as necessary. The process of forming the intermediate layer can be carried out by a method selected appropriately from known methods.

Through the above, the photosensitive member according to the second embodiment has been described. The photosensitive member according to the second embodiment is excellent in abrasion resistance.

EXAMPLES

The following provides more specific description of the present disclosure through use of Examples. However, it should be noted that the present disclosure is not limited to the scope of the Examples.

<Preparation of Polyarylate Resin>

[Preparation of Polyarylate Resin (R-1)]

A three-necked flask was used as a reaction vessel. The reaction vessel was a 1-L three-necked flask equipped with a thermometer, a three-way cock, and a 200-mL dripping funnel. Into the reaction vessel, 12.24 g (41.28 mmol) of 1,1-bis(4-hydroxy-3-methylphenyl)cyclohexane, 0.062 g (0.413 mmol) of t-butylphenol, 3.92 g (98 mmol) of sodium hydroxide, and 0.120 g (0.384 mmol) of benzyltributylammonium chloride were added. Next, the reaction vessel was purged with argon. Next, 300 mL of water was added into the reaction vessel. The internal temperature of the reaction vessel was reduced to 50° C. The reaction vessel contents were stirred for 1 hour while the internal temperature of the reaction vessel was maintained at 50° C. Thereafter, the internal temperature of the reaction vessel was reduced to 10° C. As a result, an alkaline aqueous solution was obtained.

Separately from the alkaline aqueous solution, 4.10 g (16.2 mmol) of 2,6-naphthalenedicarboxylic acid dichloride and 4.10 g (16.2 mmol) of 1,4-naphthalenedicarboxylic acid dichloride were dissolved in 150 mL of chloroform (AMYLENE (registered Japanese trademark) added). As a result, a chloroform solution was obtained.

The chloroform solution was gradually dripped into the alkaline aqueous solution through a dripping funnel over 110 minutes to initiate a polymerization reaction. The internal temperature of the reaction vessel was adjusted to 15±5° C., and the polymerization reaction was caused to proceed while the reaction vessel contents were stirred for 4 hours.

Thereafter, decantation was performed to remove an upper layer (water layer) from the reaction vessel contents to collect an organic layer. Next, 400 mL of ion exchanged water was added into a 1-L three-necked flask, and then the collected organic layer was added into the flask. Furthermore, 400 mL of chloroform and 2 mL of acetic acid were added into the flask. The three-necked flask contents were stirred at room temperature (25° C.) for 30 minutes. Thereafter, decantation was performed to remove an upper layer (water layer) from the three-necked flask contents to collect an organic layer. The collected organic layer was washed with 1 L of water five times using a separatory funnel. As a result, the water-washed organic layer was obtained.

Next, the water-washed organic layer was filtered to collect a filtrate. Into a 1-L conical flask, 1 L of methanol was added. The collected filtrate was gradually dripped into the conical flask to give a precipitate. The precipitate was filtered off. The thus collected precipitate was vacuum dried for 12 hours at 70° C. As a result, the polyarylate resin (R-1) was obtained. The mass yield of the polyarylate resin (R-1) was 12.9 g, and the percentage yield thereof was 83.5 mol %. The polyarylate resin (R-1) had a viscosity average molecular weight of 50,500.

[Preparation of Polyarylate Resins (R-2) to (R-6)]

With respect to each of the polyarylate resins (R-2) to (R-6), 1,1-bis(4-hydroxy-3-methylphenyl)cyclohexane was changed to an aromatic diol that was a starting material of the polyarylate resin. Furthermore, with respect to each of the polyarylate resins (R-5) and (R-6), the aromatic dicarboxylic acid content of the polyarylate resin was changed so as to give a specified mole fraction s/(s+u). Other than the above, the polyarylate resins (R-2) to (R-6) were prepared according to the same method as the preparation method of the polyarylate resin (R-1).

[Preparation of Polyarylate Resin (R-7)]

With respect to the polyarylate resin (R-7), 1,1-bis(4-hydroxy-3-methylphenyl)cyclohexane (41.28 mmol) was changed to 1,1-bis(4-hydroxy-3-methylphenyl)cyclohexane (20.64 mmol) and 1,1-bis(4-hydroxy-3-methylphenyl)ethane (20.64 mmol). Other than the above, the polyarylate resin (R-7) was prepared according to the same method as the preparation method of the polyarylate resin (R-1).

The viscosity average molecular weights of the polyarylate resins (R-2), (R-3), (R-4), (R-5), (R-6), and (R-7) were respectively 61,000, 52,500, 51,300, 63,200, 59,500, and 49,700.

Next, a proton nuclear magnetic resonance spectrometer (product of JASCO Corporation, 300 MHz) was used to measure $^1$H-NMR spectra of the polyarylate resins (R-1) to (R-7) prepared as described above. $CDCl_3$ was used as a solvent. Tetramethylsilane (TMS) was used as an internal standard sample. The $^1$H-NMR spectra were used to confirm that the polyarylate resins (R-1) to (R-7) were obtained.

<Production of Photosensitive Member>

[Photosensitive Member Materials]

A charge generating material, hole transport materials, and binder resins described below were prepared as materials for forming photosensitive layers of photosensitive members.

The charge generating material (CGM-2) described in association with the second embodiment was prepared. The charge generating material (CGM-2) was titanyl phthalocyanine (Y-form titanyl phthalocyanine) represented by chemical formula (CGM-2). The charge generating material (CGM-2) had a Y-form crystalline structure. The Y-form titanyl phthalocyanine was confirmed to exhibit a main peak at a Bragg angle (2θ±0.2°) of 27.2° in an X-ray diffraction spectrum thereof.

The hole transport materials (HTM-1) to (HTM-9) described in association with the second embodiment were prepared.

The polyarylate resins (R-1) to (R-7) and binder resins (R-B1) to (R-B6) were prepared. The polyarylate resins (R-1) to (R-7) were each synthesized as described above. The binder resins (R-B1) to (R-B6) are respectively represented by chemical formulae (R-B1) to (R-B6). The number attached to each repeating unit in chemical formulae (R-B1) to (R-B6) indicates the mole fraction of the repeating unit.

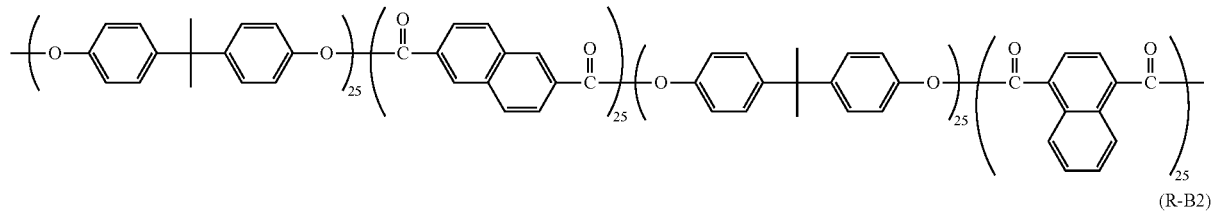

(R-B1)

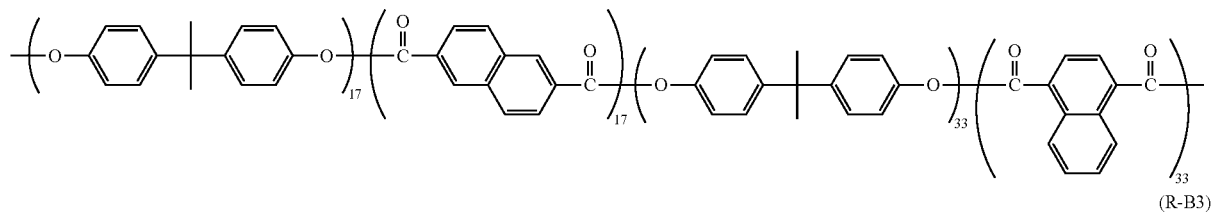

(R-B2)

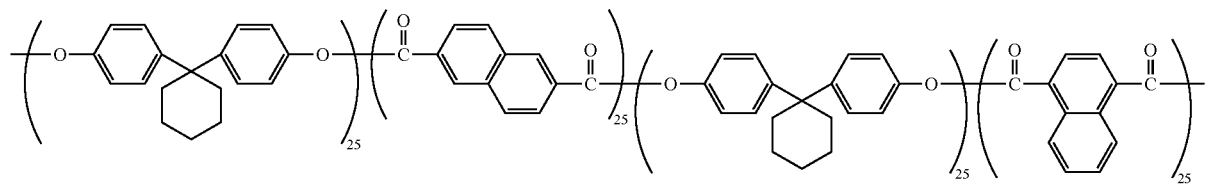

(R-B3)

(R-B4)

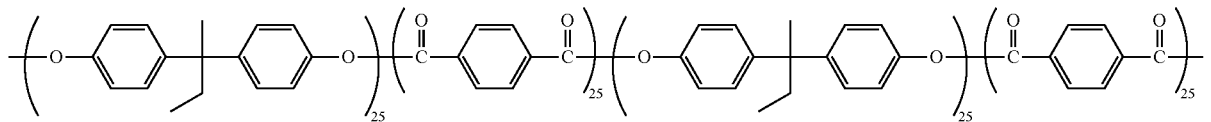

(R-B5)

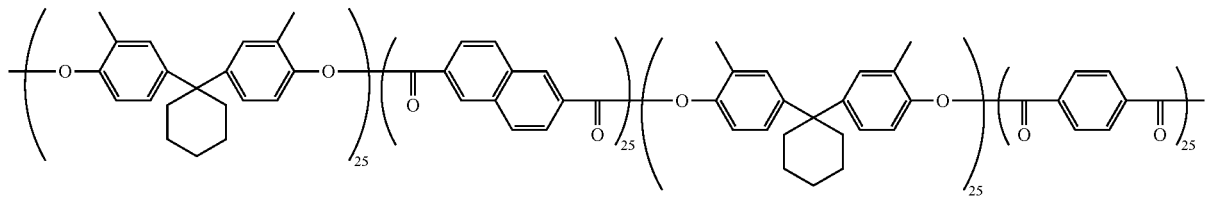

(R-B6)

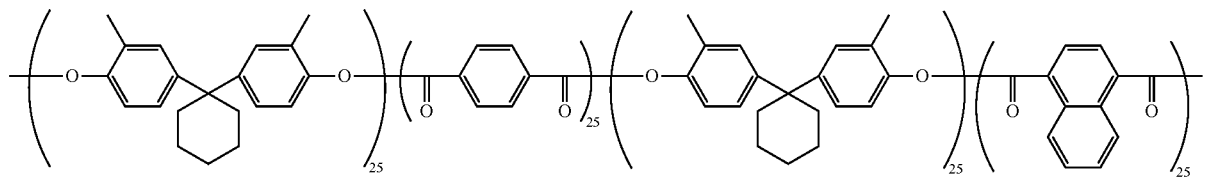

[Production of Photosensitive Member (A-1)]

The following describes production of the photosensitive member (A-1).

(Intermediate Layer Formation)

First, surface-treated titanium oxide ("test sample SMT-A", product of Tayca Corporation, average primary particle diameter 10 nm) was prepared. More specifically, titanium oxide was surface-treated using alumina and silica and was also subsequently surface-treated using methyl hydrogen polysiloxane while being subjected to wet dispersion. Next, the surface-treated titanium oxide (2 parts by mass) and AMILAN (registered Japanese trademark) ("CM8000", product of Toray Industries, Inc.), which was a polyamide resin, (1 part by mass) were added to a combined solvent. The combined solvent contained methanol (10 parts by mass), butanol (1 part by mass), and toluene (1 part by mass). The polyamide resin was a four-component copolymer polyamide resin of polyamide 6, polyamide 12, polyamide 66, and polyamide 610. A bead mill was used to mix the materials (the surface-treated titanium oxide and the polyamide resin) with the combined solvent for 5 hours to disperse the materials in the combined solvent. Thus, an application liquid for intermediate layer formation was prepared.

The application liquid for intermediate layer formation was filtered using a filter having a pore size of 5 μm. Next, the application liquid for intermediate layer formation was applied onto the surface of a conductive substrate by dip coating to form a film. The conductive substrate was an aluminum drum-shaped support (diameter 30 mm, total length 246 mm). Next, the thus formed film was dried at 130° C. for 30 minutes to form an intermediate layer (film thickness 2 μm) on the conductive substrate.

(Charge Generating Layer Formation)

The Y-form titanyl phthalocyanine (1.5 parts by mass) and a polyvinyl acetal resin ("S-LEC KX-5", product of Sekisui Chemical Co., Ltd.) (1 part by mass) as a base resin were added to a combined solvent. The combined solvent contained propylene glycol monomethyl ether (40 parts by mass) and tetrahydrofuran (40 parts by mass). A bead mill was used to mix the materials (the Y-form titanyl phthalocyanine and the polyvinyl acetal resin) with the combined solvent for 2 hours to disperse the materials in the combined solvent. Thus, an application liquid for charge generating layer formation was prepared.

The application liquid for charge generating layer formation was filtered using a filter having a pore size of 3 μm. Next, the resultant filtrate was applied by dip coating onto the intermediate layer formed as described above to form a film. The film was dried for 5 minutes at 50° C. Thus, a charge generating layer (film thickness 0.3 μm) was formed on the intermediate layer.

(Charge Transport Layer Formation)

To a combined solvent, 50 parts by mass of the hole transport material (HTM-1), 5 parts by mass of meta-terphenyl as an additive, 100 parts by mass of the polyarylate resin (R-1) (viscosity average molecular weight 50,500) as a binder resin, and 0.05 parts by mass of dimethyl silicone oil ("KF96-50CS", product of Shin-Etsu Chemical Co., Ltd.) as a leveling agent were added. The combined solvent contained 600 parts by mass of tetrahydrofuran (THF) and 100 parts by mass of toluene. The volume ratio (THF/toluene) in the combined solvent was 86/14. The materials (the hole transport material (HTM-1), the meta-terphenyl, the polyarylate resin (R-1), and the dimethyl silicone oil) were mixed with the combined solvent for 12 hours to disperse the materials in the combined solvent. Thus, an application liquid for charge transport layer formation was prepared. The thus prepared application liquid for charge transport layer formation was left to stand for 1 day.

The application liquid for charge transport layer formation was applied onto the charge generating layer in the same manner as of the application liquid for charge generating layer formation to form a film. Next, the film was dried for 70 minutes to form a charge transport layer (film thickness 20 μm) on the charge generating layer. The film was dried at a temperature raised from a starting temperature of 60° C. to an ending temperature of 130° C. at a heating rate of 1° C./minute. As a result, the photosensitive member (A-1) was obtained. The photosensitive member (A-1) had a structure in which the intermediate layer, the charge generating layer, and the charge transport layer were stacked in the stated order on the conductive substrate.

[Photosensitive Members (A-2)-(A-15), (B-1)-(B-4), and (B-8)-(B-9)]

The photosensitive members (A-2) to (A-15), (B-1) to (B-4), (B-8), and (B-9) were each produced according to the same method as the production method of the photosensitive member (A-1) in all aspects other than the following points. The hole transport material (HTM-1) was changed to another hole transport material as shown in Table 1. While the polyarylate resin (Resin-1) was used in the production of the photosensitive member (A-1), the binder resins as shown in Table 1 were used.

[Photosensitive Members (B-5)-(B-7)]

The photosensitive members (B-5) to (B-7) were each produced according to the same method as the production method of the photosensitive member (A-1) in all aspects other than the following points. A different hole transport material and a different polyarylate resin were used. Furthermore, the combined solvent (toluene and tetrahydrofuran) used as the solvent of the application liquid for charge transport layer formation was changed to chloroform. Solubility of the polyarylate resins (R-1) to (R-7) and the binder resins (R-B1) to (R-B6) in chloroform was higher than solubility thereof in the combined solvent of toluene and tetrahydrofuran.

[Evaluation of Photosensitive Member Properties]

(Electrical Characteristic Evaluation)

(Measurement of charge potential $V_0$)

With respect to each of the photosensitive members (A-1) to (A-15) and (B-1) to (B-9), a surface potential of the photosensitive member was measured using a drum sensitivity test device (product of Gen-Tech, Inc.) under conditions of a rotation speed of 31 rpm and an inflow current of −10 μmA. The thus measured surface potential was taken to be a charge potential ($V_0$). The measurement was performed under ambient conditions of 23° C. and 50% relative humidity. Table 1 shows the charge potential ($V_0$).

(Measurement of Post-Irradiation Potential $V_L$)

With respect to each of the photosensitive members (A-1) to (A-15) and (B-1) to (B-9), the photosensitive member was charged to −600 V at a rotation speed of 31 rpm using a drum sensitivity test device (product of Gen-Tech, Inc.). Next, a band pass filter was used to obtain monochromatic light (wavelength: 780 nm, light intensity 0.8 μJ/cm$^2$) from light emitted by a halogen lamp, and the surface of the photosensitive member was irradiated with the monochromatic light. The surface potential of the photosensitive member was measured 80 milliseconds after completion of irradiation with the monochromatic light. The measured surface potential was taken to be a post-irradiation potential ($V_L$). The measurement was performed under ambient conditions of 23° C. and 50% relative humidity. Table 1 shows the post-irradiation potential ($V_0$).

(Evaluation of Photosensitive Member Abrasion Resistance)

Application liquids for charge transport layer formation were prepared. The application liquids for charge transport layer formation were prepared under the same conditions as the application liquids for charge transport layer formation used in production of the respective photosensitive members (A-1) to (A-15) and (B-1) to (B-9). The application liquids for charge transport layer formation were also left to stand for 1 day. Each of the application liquids for charge transport layer formation was applied onto a polypropylene sheet (thickness 0.3 mm) wound around an aluminum pipe (diameter: 78 mm) to form a film. The film was dried for 70 minutes. The film was dried at a temperature raised from a starting temperature of 60° C. to an ending temperature of 130° C. at a heating rate of 1° C./minute. As a result, a sheet was obtained. The sheet had a charge transport layer (film thickness 30 μm) formed thereon. The charge transport layer was removed from the polypropylene sheet and mounted on a specimen mounting card S-36 (product of TABER Industries). As a result, an abrasion test sample was obtained.

The abrasion test sample was loaded in a rotary abrasion tester (product of Toyo Seiki Co., Ltd.) and subjected to 1,000 rotations using a wear ring CS-10 (product of TABER Industries) under conditions of a 500 gf load and a rotation speed of 60 rpm to perform an abrasion evaluation test. An abrasion loss (mg/1,000 rotations), which is a difference in mass of the sample before and after the abrasion evaluation test, was measured. Abrasion resistance of the corresponding photosensitive member was evaluated based on the thus obtained abrasion loss. Table 1 shows the abrasion loss.

(Evaluation of Life of Application Liquid for Charge Transport Layer Formation)

Each of the application liquids for charge transport layer formation for the photosensitive members (A-1) to (A-15) and (B-1) to (B-9) was left to stand for 1 day, and subsequently whether the application liquid for charge transport layer formation gelled or not was visually confirmed. Any gelled application liquids for charge transport layer formation were not able to form a charge transport layer. The word "Gelled" in the column under the headings "Electrical characteristics" and "Abrasion resistance" in Table 1 indicates that the corresponding application liquid for charge transport layer formation gelled after the liquid had been left to stand for 1 day. The word "Gelled" also indicates that the corresponding application liquid for charge transport layer formation was not able to form a charge transport layer, and therefore neither the electrical characteristics nor the abrasion resistance thereof was evaluable. The absence of the word "Gelled" in the column under the headings "Electrical characteristics" and "Abrasion resistance" in Table 1 indicates that the corresponding application liquid for charge transport layer formation did not gel after the liquid had been left to stand for 1 day.

Table 1 shows compositions and property evaluation results of the photosensitive members (A-1) to (A-15) and (B-1) to (B-9). In Table 1, HTM-1 to HTM-9 in the column titled "HTM" respectively represent the hole transport materials (HTM-1) to (HTM-9). R-1 to R-7 and R-B1 to R-B6 in the column titled "Resin" respectively represent the polyarylate resins (R-1) to (R-7) and the binder resins (R-B1) to (R-B6). "THF/toluene" in the column titled "Solvent in application liquid" indicates that the solvent in the corresponding application liquid for charge transport layer formation was "the combined solvent of THF and toluene". "Chloroform" in the column titled "Solvent in application liquid" indicates that the solvent in the corresponding application liquid for charge transport layer formation was "chloroform". "(86/14)" indicates that the volume ratio (THF:toluene) in the combined solvent was 86:14.

TABLE 1

| | Photosensitive member | HTM | Resin | Charge transport layer Solvent in application liquid | Electrical characteristics $V_0$ (V) | $V_L$ (V) | Abrasion resistance Abrasion loss (mg/1000 rotations) |
|---|---|---|---|---|---|---|---|
| Example 1 | A-1 | HTM-1 | R-1 | THF/toluene (86/14) | −683 | −63 | 4.3 |
| Example 2 | A-2 | HTM-2 | R-1 | THF/toluene (86/14) | −693 | −73 | 4.2 |
| Example 3 | A-3 | HTM-3 | R-1 | THF/toluene (86/14) | −656 | −68 | 4.0 |
| Example 4 | A-4 | HTM-4 | R-1 | THF/toluene (86/14) | −678 | −50 | 3.6 |

TABLE 1-continued

|  | Photosensitive member | Charge transport layer | | | Electrical characteristics | | Abrasion resistance Abrasion loss |
|---|---|---|---|---|---|---|---|
|  |  | HTM | Resin | Solvent in application liquid | $V_0$ (V) | $V_L$ (V) | (mg/1000 rotations) |
| Example 5 | A-5 | HTM-5 | R-1 | THF/toluene (86/14) | −678 | −49 | 3.9 |
| Example 6 | A-6 | HTM-6 | R-1 | THF/toluene (86/14) | −673 | −61 | 4.4 |
| Example 7 | A-7 | HTM-7 | R-1 | THF/toluene (86/14) | −678 | −60 | 4.3 |
| Example 8 | A-8 | HTM-8 | R-1 | THF/toluene (86/14) | −693 | −91 | 4.5 |
| Example 9 | A-9 | HTM-9 | R-1 | THF/toluene (86/14) | −690 | −60 | 4.8 |
| Example 10 | A-10 | HTM-3 | R-2 | THF/toluene (86/14) | −680 | −59 | 3.9 |
| Example 11 | A-11 | HTM-3 | R-3 | THF/toluene (86/14) | −674 | −57 | 4.4 |
| Example 12 | A-12 | HTM-3 | R-4 | THF/toluene (86/14) | −686 | −61 | 5.8 |
| Example 13 | A-13 | HTM-3 | R-5 | THF/toluene (86/14) | −691 | −60 | 3.6 |
| Example 14 | A-14 | HTM-3 | R-6 | THF/toluene (86/14) | −682 | −60 | 4.3 |
| Example 15 | A-15 | HTM-3 | R-7 | THF/toluene (86/14) | −683 | −64 | 5.2 |
| Comparative Example 1 | B-1 | HTM-3 | R-B1 | THF/toluene (86/14) |  | Gelled |  |
| Comparative Example 2 | B-2 | HTM-3 | R-B2 | THF/toluene (86/14) |  | Gelled |  |
| Comparative Example 3 | B-3 | HTM-3 | R-B3 | THF/toluene (86/14) |  | Gelled |  |
| Comparative Example 4 | B-4 | HTM-3 | R-B4 | THF/toluene (86/14) | −684 | −61 | 9.8 |
| Comparative Example 5 | B-5 | HTM-3 | R-B1 | Chloroform | −694 | −79 | 9.3 |
| Comparative Example 6 | B-6 | HTM-3 | R-B2 | Chloroform | −675 | −72 | 10.1 |
| Comparative Example 7 | B-7 | HTM-3 | R-B3 | Chloroform |  | Gelled |  |
| Comparative Example 8 | B-8 | HTM-3 | R-B5 | THF/toluene (86/14) |  | Gelled |  |
| Comparative Example 9 | B-9 | HTM-3 | R-B6 | THF/toluene (86/14) | −678 | −70 | 8.4 |

As shown in Table 1, the charge transport layer of each of the photosensitive members (A-1) to (A-15) contained any one of the polyarylate resins (R-1) to (R-7) as a binder resin. The polyarylate resins (R-1) to (R-7) were encompassed by general formula (1). As shown in Table 1, the photosensitive members (A-1) to (A-15) each resulted in an abrasion loss of from 3.6 mg to 5.8 mg.

As shown in Table 1, the charge transport layer of each of the photosensitive members (B-1) to (B-9) contained any one of the binder resins (R-B1) to (R-B6). The binder resins (R-B1) to (R-B6) were not encompassed by general formula (1). As shown in Table 1, the photosensitive members (B-4) to (B-6) and (B-9) each resulted in an abrasion loss of from 8.4 mg to 10.1 mg. The application liquids for charge transport layer formation for the photosensitive members (B-1) to (B-3), (B-7), and (B-8) each gelled, failing to form a photosensitive layer. Consequently, abrasion resistance of the photosensitive members (B-1) to (B-3), (B-7), and (B-8) was not evaluable.

As apparent from Table 1, the polyarylate resins (R-1) to (R-7) impart excellent abrasion resistance to the photosensitive members compared to the binder resins (R-B1) to (R-B6). It is also apparent that the photosensitive members (A-1) to (A-15) have higher abrasion resistance than the photosensitive members (B-1) to (B-9).

As shown in Table 1, the photosensitive layer of each of the photosensitive members (A-3), (A-10), (A-11), (A-13), and (A-14) contained any one of the polyarylate resins (R-1) to (R-3), (R-5), and (R-6) as a binder resin. All of the polyarylate resins (R-1) to (R-3), (R-5), and (R-6) were polyarylate resins represented by general formula (1) in which $R^2$ and $R^3$ each represent an alkyl group having a carbon number of at least 1 and no greater than 4. The photosensitive members (A-3), (A-10), (A-11), (A-13), and (A-14) each resulted in an abrasion loss of from 3.6 mg to 4.4 mg.

As shown in Table 1, the photosensitive layer of the photosensitive member (A-12) contained the polyarylate resin (R-4) as a binder resin. The polyarylate resin (R-4) was not a polyarylate resin represented by general formula (1) in which $R^2$ and $R^3$ each represent an alkyl group having a carbon number of at least 1 and no greater than 4. The photosensitive member (A-12) resulted in an abrasion loss of 5.8 mg.

It is apparent that the polyarylate resins (R-1) to (R-3), (R-5), and (R-6) improve abrasion resistance of photosensitive members more than the polyarylate resin (R-4). It is apparent that the photosensitive members (A-3), (A-10), (A-11), (A-13), and (A-14) have higher abrasion resistance than the photosensitive member (A-12) as each having resulted in a smaller abrasion loss than the photosensitive member (A-12).

What is claimed is:

1. A polyarylate resin represented by general formula (1) shown below

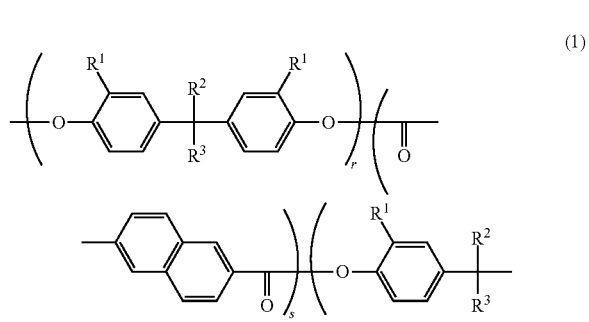

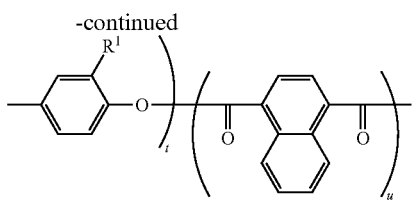

wherein in general formula (1),
$R^1$ represents a hydrogen atom or a methyl group,
$R^2$ and $R^3$ each represent a hydrogen atom or an alkyl group having a carbon number of at least 1 and no greater than 4,
$R^2$ and $R^3$ are not the same as one another,
when $R^1$ represents a hydrogen atom, $R^2$ and $R^3$ are not bonded to one another,
when $R^1$ represents a methyl group, $R^2$ and $R^3$ are optionally bonded to one another to form a ring,
r and s each represent a number greater than or equal to 0 and less than or equal to 49,
t and u each represent a number greater than or equal to 1 and less than or equal to 50,
$r+s+t+u=100$, and
$r+t=s+u$.

2. The polyarylate resin according to claim 1, wherein in general formula (1),
$R^2$ and $R^3$ each represent an alkyl group having a carbon number of at least 1 and no greater than 4.

3. The polyarylate resin according to claim 1, wherein in general formula (1),
one of $R^2$ and $R^3$ represents a methyl group, and
the other of $R^2$ and $R^3$ represents an ethyl group.

4. The polyarylate resin according to claim 1, wherein in general formula (1),
$R^1$ represents a methyl group, and
$R^2$ and $R^3$ are bonded to one another to represent a cycloalkylidene group having a carbon number of at least 5 and no greater than 7.

5. The polyarylate resin according to claim 1, wherein in general formula (1),
$s/(s+u)$ is at least 0.30 and no greater than 0.70.

6. The polyarylate resin according to claim 1, wherein general formula (1) is represented by chemical formula (R-1), chemical formula (R-2), chemical formula (R-3), chemical formula (R-4), chemical formula (R-5), chemical formula (R-6), or chemical formula (R-7) shown below.

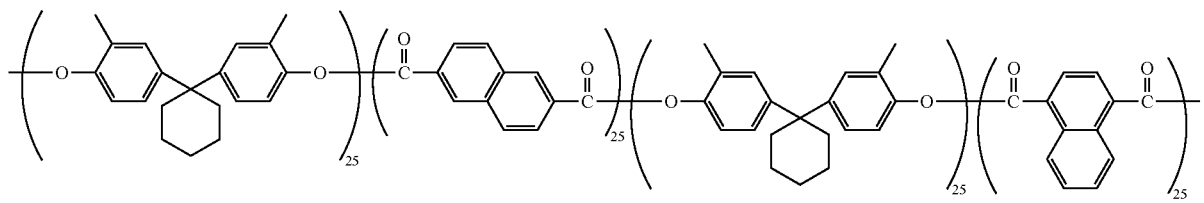

(R-1)

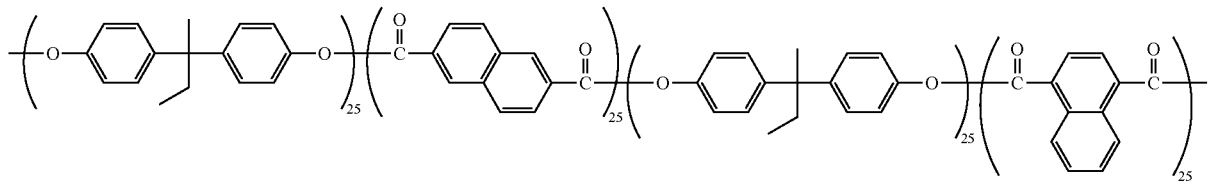

(R-2)

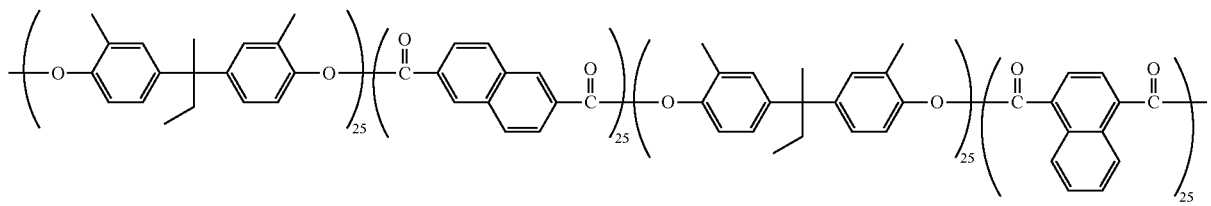

(R-3)

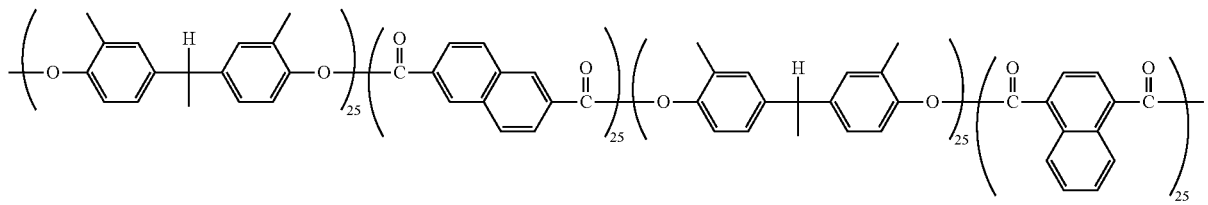

(R-4)

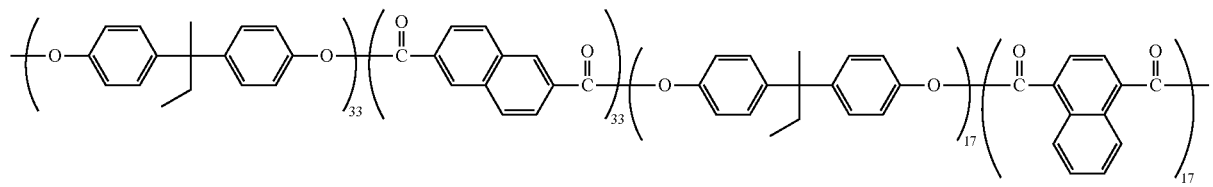

(R-5)

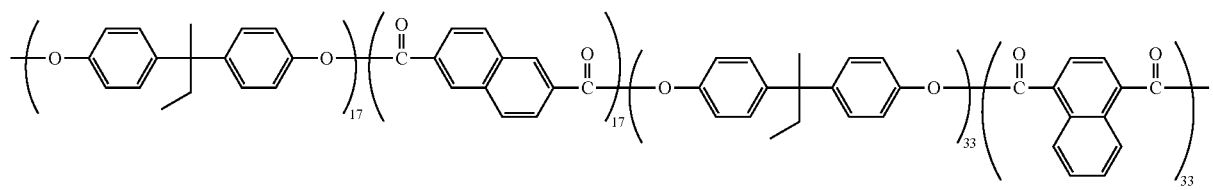

(R-6)

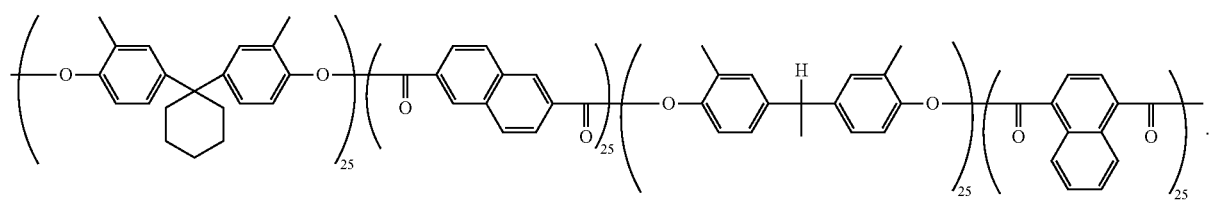

(R-7)

7. An electrophotographic photosensitive member comprising:
a conductive substrate; and
a photosensitive layer, wherein
the photosensitive layer contains a charge generating material, a hole transport material, and a binder resin, and
the binder resin includes the polyarylate resin according to claim 1.

8. The electrophotographic photosensitive member according to claim 7, wherein
the hole transport material includes a compound represented by general formula (2), (3), or (4) shown below (2)

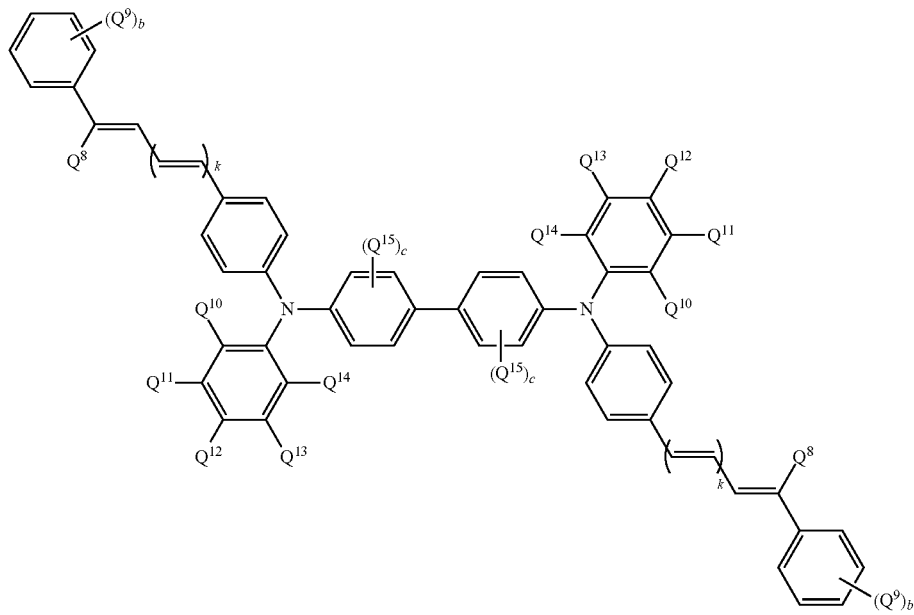

(3)

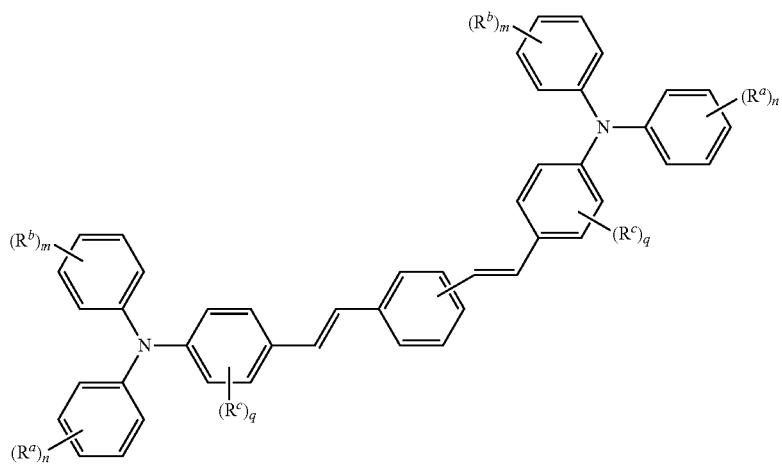

(4)

wherein in general formula (2), $Q^1$ represents a hydrogen atom, an alkyl group having a carbon number of at least 1 and no greater than 8, an alkoxy group having a carbon number of at least 1 and no greater than 8, or a phenyl group optionally substituted with an alkyl group having a carbon number of at least 1 and no greater than 8, $Q^2$ represents an alkyl group having a carbon number of at least 1 and no greater than 8, an alkoxy group having a carbon number of at least 1 and no greater than 8, or a phenyl group, $Q^3$, $Q^4$, $Q^5$, $Q^6$, and $Q^7$ each represent, independently of one another, a hydrogen atom, an alkyl group having a carbon number of at least 1 and no greater than 8, an alkoxy group having a carbon number of at least 1 and no greater than 8, or a phenyl group, adjacent two members among $Q^3$, $Q^4$, $Q^5$, $Q^6$, and $Q^7$ are optionally bonded to one another to form a ring, a represents an integer of at least 0 and no greater than 5, and when a represents an integer of at least 2 and no greater than 5, chemical groups $Q^2$ bonded to the same phenyl group may be the same as or different from one another, in general formula (3), $Q^8$, $Q^{10}$, $Q^{11}$, $Q^{12}$, $Q^{13}$, and $Q^{14}$ each represent, independently of one another, a hydrogen atom, an alkyl group having a carbon number of at least 1 and no greater than 8, an alkoxy group having a carbon number of at least 1 and no greater than 8, or a phenyl group, $Q^9$ and $Q^{15}$ each represent, independently of one another, an alkyl group having a carbon number of at least 1 and no greater than 8, an alkoxy group having a carbon number of at least 1 and no greater than 8, or a phenyl group, b represents an integer of at least 0 and no greater than 5, when b represents an integer of at least 2 and no greater than 5, chemical groups $Q^9$ bonded to the same phenyl group may be the same as or different from one another, c represents an integer of at least 0 and no greater than 4, when c represents an integer of at least 2 and no greater than 4, chemical groups $Q^{15}$ bonded to the same phenyl group may be the same as or different from one another, and k represents 0 or 1, and in general formula (4), $R^a$, $R^b$, and $R^c$ each represent, independently of one another, an alkyl group having a carbon number of at least 1 and no greater than 8, a phenyl group, or an alkoxy group having a carbon number of at least 1 and no greater than 8, q represents an integer of at least 0 and no greater than 4, when q represents an integer of at least 2 and no greater than 4, chemical groups $R^c$ bonded to the same phenyl group may be the same as or different from one another, m and n each represent, independently of one another, an integer of at least 0 and no greater than 5, when m represents an integer of at least 2 and no greater than 5, chemical groups $R^b$ bonded to the same phenyl group may be the same as or different from one another, and when n represents an integer of at least 2 and no greater than 5, chemical groups $R^a$ bonded to the same phenyl group may be the same as or different from one another.

9. The electrophotographic photosensitive member according to claim 8, wherein in general formula (2), $Q^1$ represents a hydrogen atom or a phenyl group substituted with an alkyl group having a carbon number of at least 1 and no greater than 8, $Q^2$ represents an alkyl group having a carbon number of at least 1 and no greater than 8, $Q^3$, $Q^4$, $Q^5$, $Q^6$, and $Q^7$ each represent, independently of one another, a hydrogen atom, an alkyl group having a carbon number of at least 1 and no greater than 8, or an alkoxy group having a carbon number of at least 1 and no greater than 8, adjacent two members among $Q^3$, $Q^4$, $Q^5$, $Q^6$, and $Q^7$ are optionally bonded to one another to form a ring, and a represents 0 or 1, in general formula (3), $Q^8$, $Q^{10}$, $Q^{11}$, $Q^{12}$, $Q^{13}$, and $Q^{14}$ each represent, independently of one another, a hydrogen atom, an alkyl group having a carbon number of at least 1 and no greater than 4, or a phenyl group, b and c each represent 0, and k represents 0 or 1, and in general formula (4), $R^a$ and $R^b$ each represent, independently of one another, an alkyl group having a carbon number of at least 1 and no greater than 4, m and n each represent, independently of one another, an integer of at least 0 and no greater than 2, and q represents 0.

10. The electrophotographic photosensitive member according to claim 8, wherein the hole transport material includes a compound represented by chemical formula (HTM-1), chemical formula (HTM-2), chemical formula (HTM-3), chemical formula (HTM-4), chemical formula (HTM-5), chemical formula (HTM-6), chemical formula (HTM-7), chemical formula (HTM-8), or chemical formula (HTM-9) shown below.

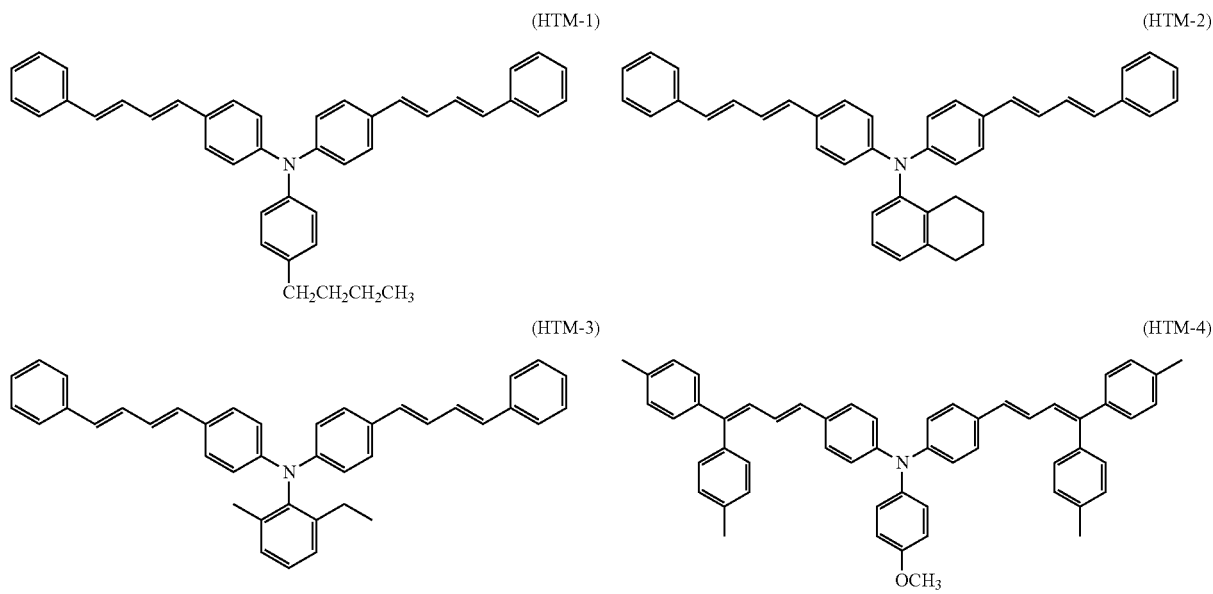

(HTM-5)

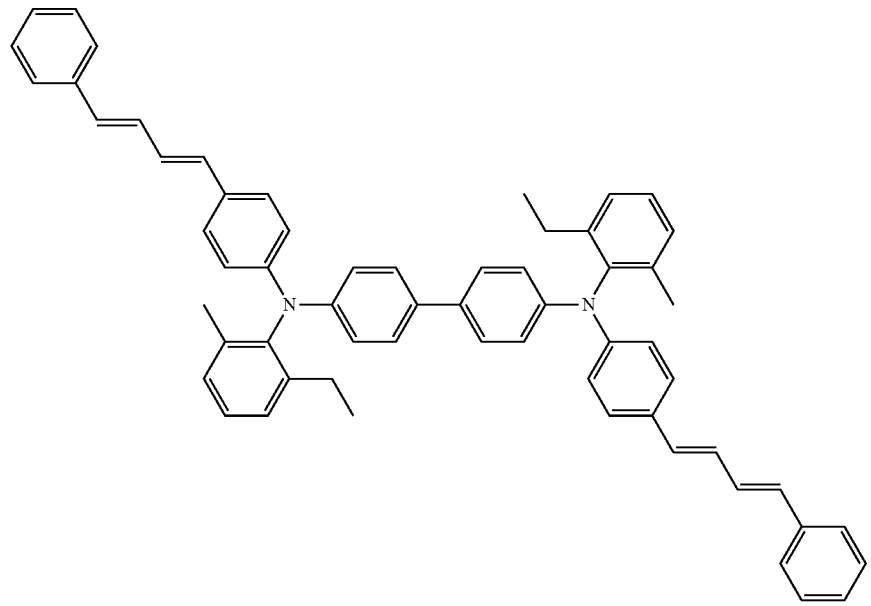

(HTM-6)

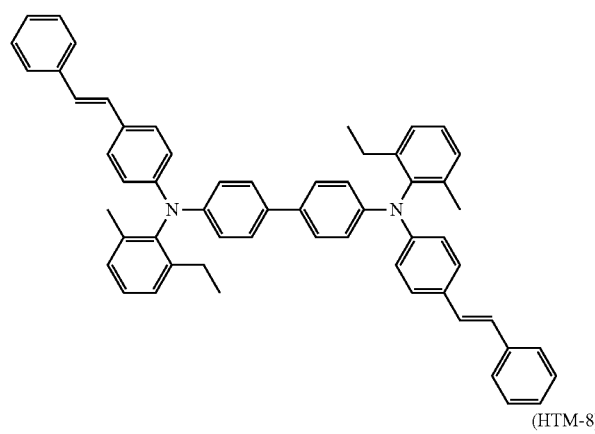

(HTM-7)

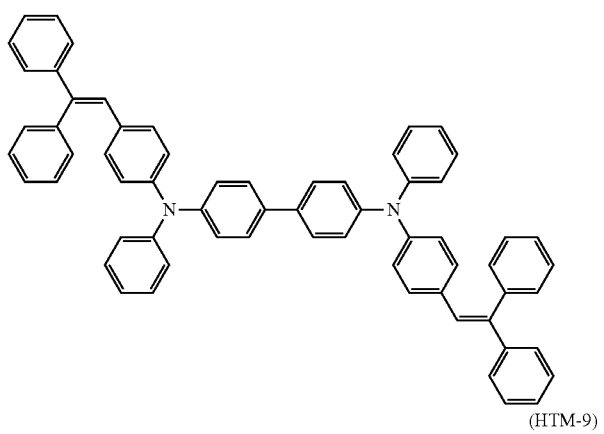

(HTM-8)

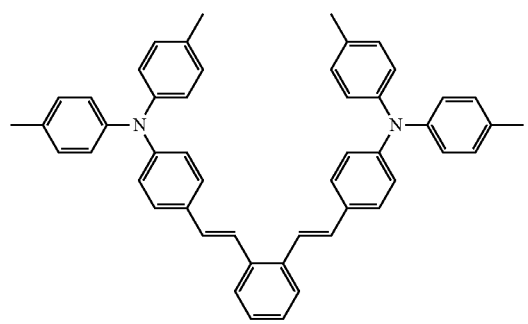

(HTM-9)

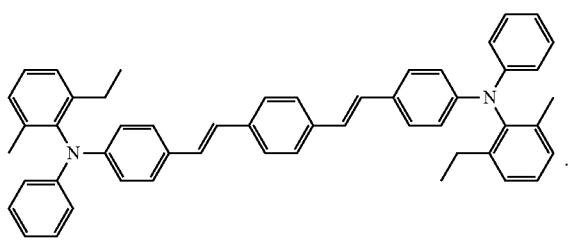

11. The electrophotographic photosensitive member according to claim 7, wherein
the photosensitive layer includes:
 a charge generating layer containing the charge generating material; and
 a charge transport layer containing the hole transport material and the binder resin, and
the charge transport layer is a one-layer charge transport layer provided as an outermost layer.

* * * * *